(12) United States Patent
Barnell et al.

(10) Patent No.: US 11,479,824 B2
(45) Date of Patent: *Oct. 25, 2022

(54) DETECTION METHOD FOR CANCER USING RNA BIOMARKERS

(71) Applicant: GENEOSCOPY, INC., St. Louis, MO (US)

(72) Inventors: Andrew Barnell, St. Louis, MO (US); Erica Barnell, St. Louis, MO (US); Yiming Kang, Clayton, MO (US); Elizabeth Wurtzler, St. Louis, MO (US); Katie Campbell, St. Louis, MO (US)

(73) Assignee: GENEOSCOPY, INC., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/578,523

(22) Filed: Jan. 19, 2022

(65) Prior Publication Data

US 2022/0154291 A1    May 19, 2022

Related U.S. Application Data

(63) Continuation of application No. 15/734,170, filed as application No. PCT/US2019/035061 on May 31, 2019.

(60) Provisional application No. 62/797,763, filed on Jan. 28, 2019, provisional application No. 62/679,621, filed on Jun. 1, 2018.

(51) Int. Cl.
*C12Q 1/6886* (2018.01)
*G01N 33/574* (2006.01)

(52) U.S. Cl.
CPC ..... *C12Q 1/6886* (2013.01); *G01N 33/57419* (2013.01); *C12Q 2600/106* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 8,067,190 B2 | 11/2011 | Uhlen et al. | |
| 2007/0172857 A1 | 7/2007 | Daito et al. | |
| 2008/0145932 A1 | 6/2008 | Matsumura et al. | |
| 2010/0112713 A1 | 5/2010 | Chapkin et al. | |
| 2010/0196889 A1 | 8/2010 | Bankaitis-Davis et al. | |
| 2010/0233712 A1 | 9/2010 | Wang et al. | |
| 2011/0060137 A1 | 3/2011 | Tanigami et al. | |
| 2011/0183332 A1 | 7/2011 | Nagaoka et al. | |
| 2012/0064525 A1 | 3/2012 | Asakura et al. | |
| 2012/0064535 A1 | 3/2012 | Tanigami et al. | |
| 2012/0196827 A1 | 8/2012 | Van Criekinge et al. | |
| 2013/0296191 A1 | 11/2013 | Roepman et al. | |
| 2013/0303398 A1 | 11/2013 | Panja | |
| 2014/0221244 A1 | 8/2014 | Chapman et al. | |
| 2018/0282815 A1* | 10/2018 | Barnell | C12Q 1/6886 |
| 2019/0271046 A1* | 9/2019 | Barnell | G01N 33/57446 |
| 2020/0040405 A1 | 2/2020 | Barnell et al. | |

FOREIGN PATENT DOCUMENTS

| | | |
|---|---|---|
| JP | 2007175021 | 7/2007 |
| JP | 2012073260 | 1/2013 |
| WO | 2008093530 | 8/2008 |
| WO | 2010010914 | 1/2010 |
| WO | 2010134245 | 11/2010 |
| WO | 2010134246 | 11/2010 |
| WO | 2014160753 | 10/2014 |
| WO | 2015017537 | 2/2015 |
| WO | 2016176446 | 11/2016 |
| WO | 2018081580 | 5/2018 |
| WO | WO-2018081580 A1 * | 5/2018 ......... C12N 15/1003 |

OTHER PUBLICATIONS

Yu et al (Cellular and Molecular Gastroenterology and Hepatology, 2016, 2:158-174).*
Written Opinion of the International Searching Authority for PCT/US2016/029777, dated Dec. 8, 2016.
Virag, P. et al., "Oxaliplatin induces different cellular and molecular chemoresistance patterns in colorectal cancer cell lines of identical origins," 2013, BMC Genomics, 14(480) pp. 1-16.
Zhai, H. et al., "Inhibition of autophagy and tumor growth in colon cancer by miR-502," 2013, Oncogene, 32, pp. 1570-1579.
Llosa, N.J. et al., "Immune checkpoints expression in MSI versus MSS colorectal cancers and their potential therapeutic implications," 2014, Journal of Clinical Oncology, 32(15) pp. suppl, 3620.
Ahmed, F.E. et al., "Diagnostic MicroRNA Markers to Screen for Sporadic Human Colon Cancer in Stool: I. Proof of Principle," 2013, Cancer Genomics & Proteomics, 10, pp. 93-114.
Barresi, V. et al., "Transcriptome analysis of copper homeostasis genes reveals coordinated upregulation of SLC31A1, SCO1, and COX11 in colorectal cancer," 2016, FEBS Open Bio, 6, pp. 794-806.
International Search Report for PCT/US2017/058789 dated Feb. 14, 2018.
Yu, J., et al., "Environmental Enteric Dysfunction Includes a Broad Spectrum of Inflammatory Responses and Epithelial Repair Processes," 2016, CMGH Cellular and Molecular Gastronenterology and Hepatology, 2(2) pp. 158-174.

(Continued)

*Primary Examiner* — Laura B Goddard

(74) *Attorney, Agent, or Firm* — Barnes & Thornburg LLP

(57) ABSTRACT

Provided herein are materials and methods for detecting colorectal neoplasms and colon cancer based on the expression levels of stool-derived eukaryotic RNA biomarkers in eukaryotic nucleic acid present in a stool sample from a subject, for example, a patient. The methods can be used for the detection of high-risk adenomas and colorectal neoplasm molecular subtypes.

28 Claims, 21 Drawing Sheets

(56) References Cited

OTHER PUBLICATIONS

Anonymous, "NucliSENS Lysis Buffer," Jan. 1, 2015, Retrieved from the Internet: https://pr.vwr.com/assetsvc/asset/en_US/id/18715711/contents.
Stauber, J. et al., "Droplet digital PCR quantities host inflammatory transcripts in feces reliably and reproducibly," 2016, Cellular Immunology, 303, pp. 43-49.
Nechvatal, et al., "Fecal collection, ambient preservation and DNA extraction for PCR amplification of bacterial and human markers from human feces," 2007, Journal of Microbiological Methods, 72(2) pp. 124-132.
Bernal, G., "Use of RNA isolated from feces as a promising tool for the early detection of colorectal cancer," 2012, International Journal of Biological Markers, 27(2) 82-9.
Maeda, S. et al., "Decreased Immunoglobulin A Concentrations in Feces, Duodenum, and Peripheral Blood Mononuclear Cells of Dogs with Inflammatory Bowel Disease," 2013, Journal Vet. Intern. Medicine, 27, pp. 47-55.
International Search Report dated Sep. 25, 2019 for corresponding International Application No. PCT/US2019/035061.
Written Opinion dated Sep. 25, 2019 for corresponding International Application No. PCT/US2019/035061.

\* cited by examiner

FIGS. 1A-AB
FIG. 1A
FIG. 1B
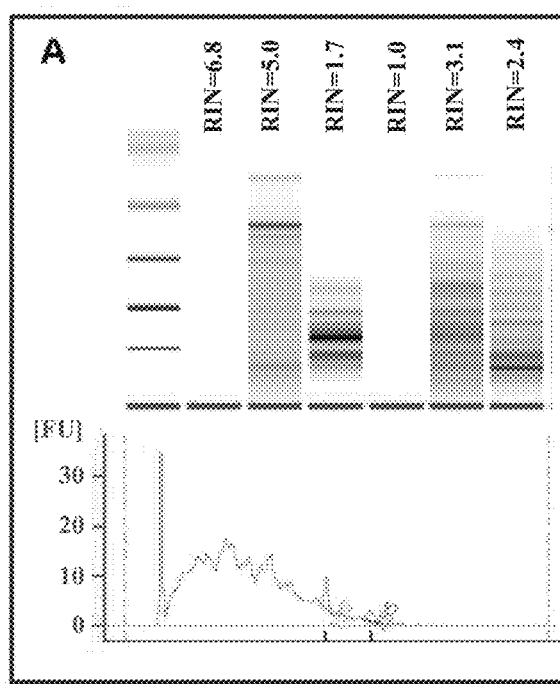
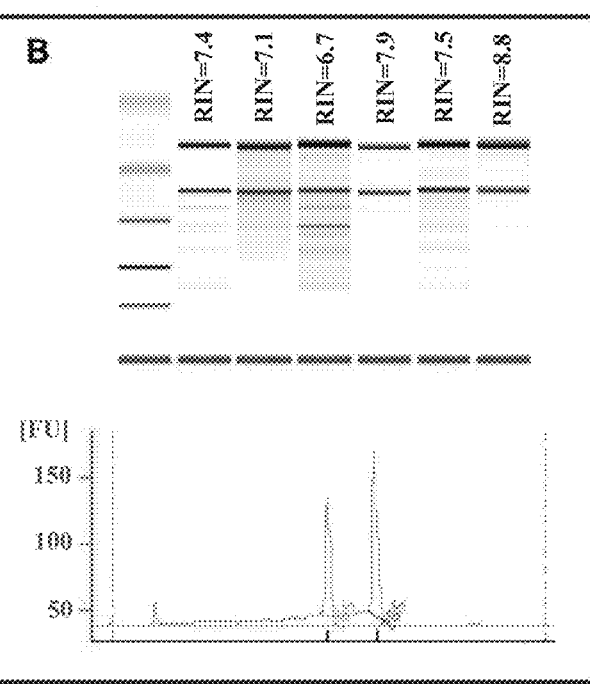

FIGS. 2A-2C
FIG. 2A
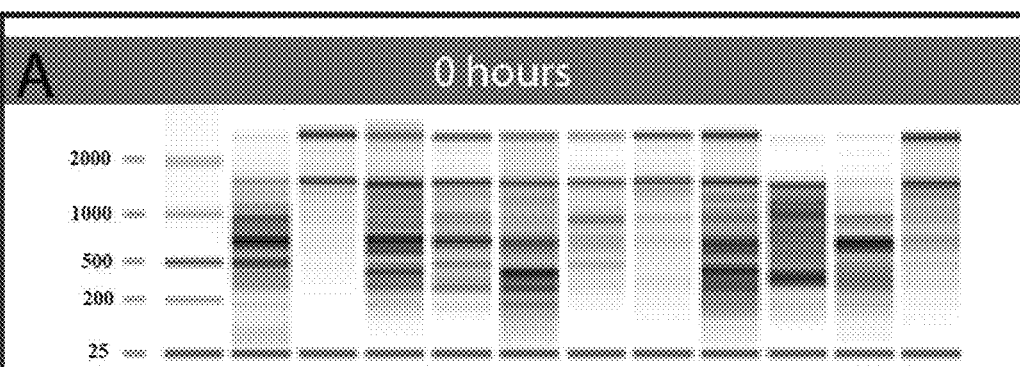
FIG. 2B
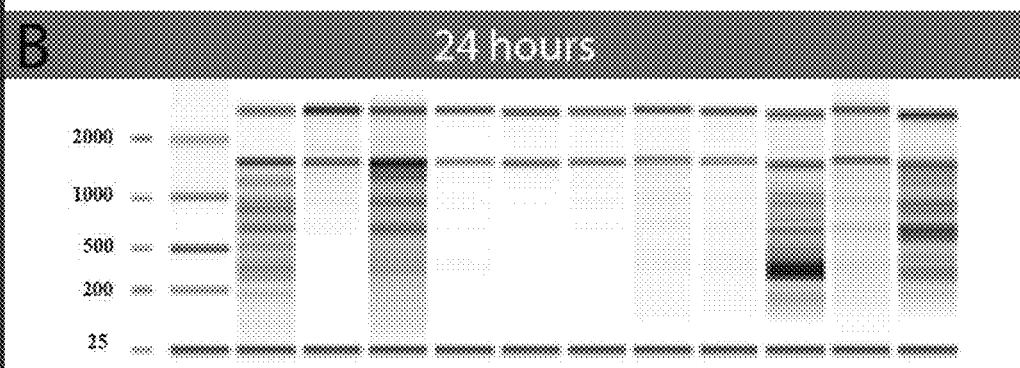
FIG. 2C
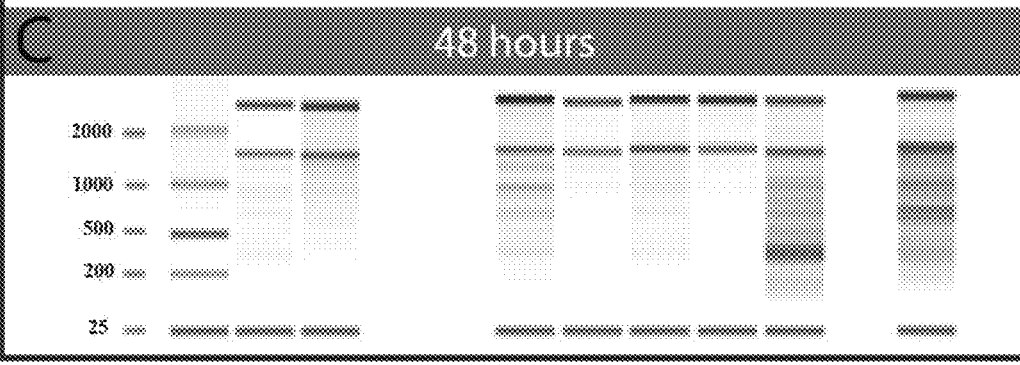

| | | | | | | |
|---|---|---|---|---|---|---|
| SFRP2 | BGN | LUM | AKT3 | SSPN | MEIS2 | IGFBP7 |
| GAS1 | PCDH7 | BNC2 | OGN | CDH11 | COL14A1 | MYO5A |
| CYP1B1 | FCGBP | COL8A2 | ASCL2 | ACTA2 | FCGR2B | CEL |
| FNDC1 | MAP1B | SPARCL1 | IGF1 | MRC1 | EGR2 | TCF4 |
| CCDC80 | FBN1 | TNS1 | DUSP4 | SPART | PALLD | RECK |
| SPOCK1 | COL6A2 | AKAP12 | JCAD | DACT3 | HOXC6 | MFAP4 |
| RETNLB | CTHRC1 | COL1A2 | ZEB1 | DAPK1 | MPDZ | DES |
| PRELP | EFEMP1 | FAM129A | GSDME | TCEAL7 | RARRES2 | MXD1 |
| SFRP4 | FBLN1 | NOX4 | APOO | TMEM47 | INHBA | VIM |
| PLN | TIMP2 | HSPB8 | HSD17B6 | TSPAN6 | TRPS1 | AHNAK2 |
| ASPN | FRMD6 | ANTXR1 | PDGFC | RUNX1T1 | MCC | TRPC1 |
| MFAP5 | PTGIS | CFH | ZFHX4 | BASP1 | TIMP3 | ZEB2 |
| DCN | FABP4 | DPT | CDH2 | CYR61 | COL6A1 | ATP8B2 |
| THBS2 | AEBP1 | VGLL3 | CHRDL1 | FGFR1 | HSPB7 | TNFAIP6 |
| THBS4 | AOC3 | B3GNT6 | NON | MYLK | TSPYL5 | DZIP1 |
| GFPT2 | EFEMP2 | LAYN | VCAN | SYNM | FBLN5 | ANGPTL2 |
| MYL9 | POU3M3 | MXRA8 | POSTN | CAVIN1 | MYH10 | C3 |
| SLIT2 | NEXN | TWIST1 | FHL1 | PDGFRL | KCNMB1 | RBMS1 |
| HOPX | TRIM7 | CALD1 | ANK2 | MAFB | LGALS1 | COL3A1 |
| ECM2 | C7 | OLFML2B | MMP2 | CPXM2 | ITGA5 | LRCH2 |
| TAGLN | MITF | AXIN2 | COL15A1 | MRC2 | PEG3 | CMTM3 |
| COL8A1 | SERPING1 | C1S | UBE2E2 | F13A1 | MN1 | GNG4 |
| CLDN11 | RAB31 | PRKD1 | CTGF | NR3C1 | RNF43 | VSIG4 |
| MGP | HMCN1 | CNRIP1 | SFRP1 | TFAP2A | UCHL1 | NPR3 |
| DDR2 | FXYD6 | CLIP4 | PRICKLE2 | COX7A1 | ACE2 | GUCY1B1 |
| FAP | FERMT2 | MXRA5 | GLI3 | PCOLCE | ITGAM | THY1 |
| ZFPM2 | AMOTL1 | ZNF521 | WWTR1 | IGFBP5 | JAM3 | NUAK1 |
| CACNA2D1 | NTM | MEIS1 | RERG | EREG | CCL2 | SYNC |
| COLEC12 | ISLR | COL5A1 | LITD1 | TRIB2 | MEOX2 | S1PR3 |
| COL10A1 | HTRA1 | HTR2B | SGCE | OMD | PLEKHO1 | GNLY |
| OLP | CRYAB | CYBRD1 | SULF1 | PXDN | TPM2 | GNG11 |
| BOC | SPARC | LOXL1 | IL1R1 | ALOX5 | BASSF8 | CYP2B6 |
| MSRB3 | ADAM12 | EFS | COL6A3 | GPC6 | PLXDC2 | SLC5A6 |
| DPYSL3 | VAV3 | RLPP4 | PHLDB2 | MYH11 | WISP1 | MRVI1 |
| ISM1 | SERPINF1 | NAP1L3 | ITGBL1 | GLS2 | BCAT1 | MLLT11 |
| PRICKLE1 | CXCL12 | TMEM45A | QPRT | LOX | FITM2 | SNAI2 |
| CNN1 | C1R | ARMCX1 | GLT8D2 | MUC2 | FN1 | SPINK4 |
| TUBB6 | COL5A2 | FLNA | PPP1R3C | GREM1 | REG4 | HEPACAM2 |
| PRRX1 | SRPX | GPNMB | LMOD1 | AC243948.1 | GPR143 | GUCY1A1 |
| STON1 | | | | | | |

QPRT
RNF43
TFAP2A
TSPAN6
TRIM7
GNLY
AXIN2
FITM2
GNG4
VAV3
RETNLB
DUSP4
TNFAIP6
HOXC6
TRIB2
CEL
GPR143
ASCL2
SLC5A6
GAS1
B3GNT6
CYP2B6
BCAT1
FAP
BOC

FIG. 9

| APC | SMAD4 | CDKN2A | BRAF |
|---|---|---|---|
| KRAS | MLH1 | CDH1 | MAKP3 |
| TP53 | CTNNB1 | PIK3CA | NRAS |
| BMP3 | EGFR | PTEN | |
| NDRG4 | BRCA1 | VEGFA | |

FIG. 10

| Category | Description | Prospective training set | Prospective hold out test set | Retrospective hold out test set | Total |
|---|---|---|---|---|---|
| Cancer (1.0) | Stage I-IV colorectal cancer | 0 | 0 | 11 | 11 |
| High-risk adenoma (2.1) | Adenoma with carcinoma in situ/high grade dysplasia, any size | 1 | 2 | 0 | 3 |
| High-risk adenoma (2.2) | Adenoma, villous growth pattern (>=25%), any size | 4 | 2 | 0 | 6 |
| High-risk adenoma (2.3) | Adenoma, >=1.0 cm in size | 5 | 5 | 0 | 10 |
| High-risk adenoma (2.4) | Serrated lesion, >=1.0 cm in size | 5 | 2 | 0 | 7 |
| Medium-risk adenoma (3) | 1 or 2 adenoma(s), >5 mm in size, and <1.0 cm in size, non-advanced | 11 | 9 | 0 | 20 |
| Medium-risk adenoma (4) | >= 3 adenomas, <1.0 cm in size, non-advanced | 10 | 7 | 0 | 17 |
| Low-risk adenoma (5) | 1 or 2 adenoma(s), <=5 mm in size, non-advanced | 37 | 24 | 0 | 61 |
| Benign polyps (6.1) | Hyperplastic, benign polyp(s) | 26 | 24 | 0 | 50 |
| Negative (6.2) | No findings on a colonoscopy | 55 | 35 | 0 | 90 |
| Total | | 154 | 110 | 11 | 275 |

FIG. 10 - CONTINUED

| Category | Description | Training set | Completed hold out test set | p-value* |
|---|---|---|---|---|
| Demographics | Gender (Female vs. male) | 63.0% | 62.0% | 0.87 |
| | Age | 52.8 ± 6.4 | 54.3 ± 7.4 | 0.07 |
| | Ethnic background (white vs. other) | 54.5% | 44.6% | 0.10 |
| | Smoking status (never smoker vs. other) | 70.1% | 66.9% | 0.57 |
| | Family history (negative family history vs. others) | 70.1% | 76.0% | 0.28 |

| Category | Description | Training set | Completed hold out test set | p-value* |
|---|---|---|---|---|
| Processing metrics | Average stool input (grams) | 12.9 ± 3.2 | 12.0 ± 3.4 | 0.03 |
| | Average RNA Integrity Value (RIN) | 4.6 ± 1.2 | 4.4 ± 1.6 | 0.18 |
| | Average RNA concentration – Qubit (ng/uL) | 168.6 ± 139.8 | 56.1 ± 79.3 | <0.01 |
| | Average fragment size (bps) | 200.6 ± 9.6 | 192.2 ± 16.8 | <0.01 |
| | Total library quantity (ng) | 29.7 ± 29.5 | 32.8 ± 64.1 | 0.60 |

*significant change in frequency was calculated using a two-tailed chi square test
*significant change in population mean was calculated using a two-tailed t-test

FIG. 14

| Feature | Feature Type | Importance |
|---|---|---|
| ACY1 | Normalized expression | 0.134 |
| TNFRSF10B | Normalized expression | 0.130 |
| DST | Normalized expression | 0.091 |
| GAPDH | Raw expression | 0.087 |
| EDN1 | Normalized expression | 0.079 |
| EGLN2 | Normalized expression | 0.074 |
| Age | Demographic information | 0.073 |
| ACHE | Normalized expression | 0.068 |
| Smoking status | Demographic information | 0.060 |
| ERBB2 | Normalized expression | 0.055 |
| SMAD4 | Normalized expression | 0.054 |
| CTNNB1 | Normalized expression | 0.050 |
| PER3 | Normalized expression | 0.045 |

FIGS. 15A-15B
FIG. 15A
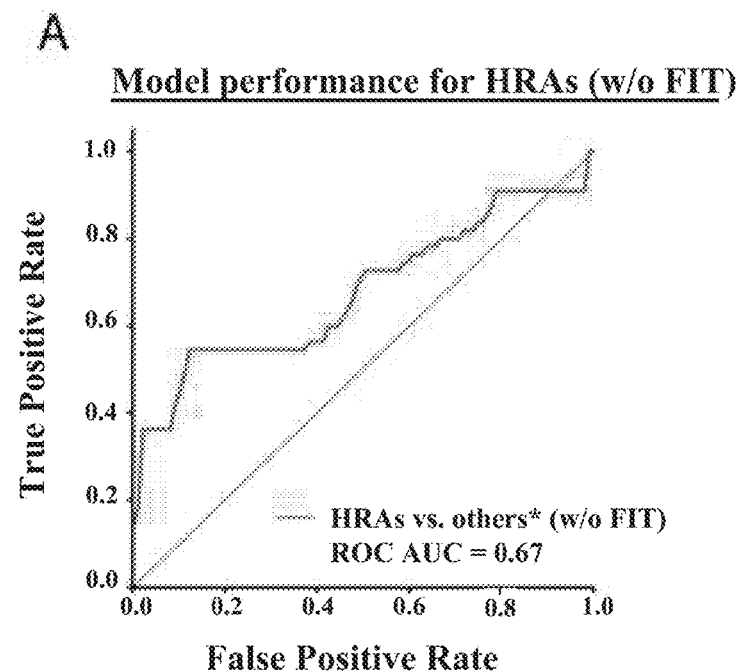
*medium-, and low-risk adenomas, benign polyps, and no findings
FIG. 15B
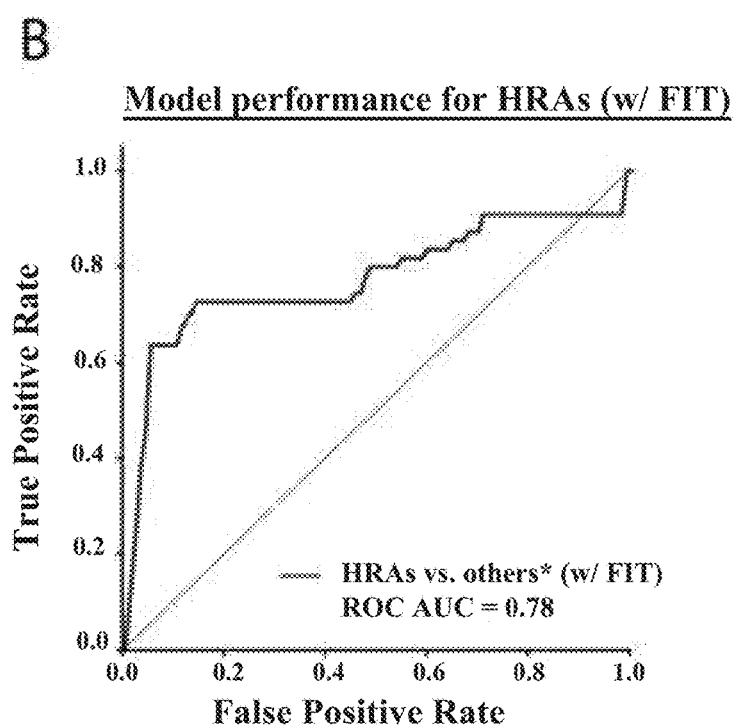
*medium-, and low-risk adenomas, benign polyps, and no findings

DETECTION METHOD FOR CANCER USING RNA BIOMARKERS

CROSS-REFERENCE TO RELATED APPLICATIONS

This application is a continuation application of U.S. patent application Ser. No. 15/734,170, filed on Dec. 1, 2020, which is the U.S. national phase of PCT/US2019/035061, filed on May 31, 2019, which claims the benefit of the filing dates of U.S. Provisional Application Ser. No. 62/679,621, filed Jun. 1, 2018, and U.S. Provisional Application Ser. No. 62/797,763, filed Jan. 28, 2019, the disclosures of all which are herein expressly incorporated by reference in their entirety.

FIELD OF THE INVENTION

The present invention relates to the extraction of eukaryotic nucleic acids from stool samples and the use of the nucleic acids for diagnosis and treatment of intestinal disease.

BACKGROUND

Gastrointestinal disorders, for example gastrointestinal cancer and other digestive diseases such as ulcerative colitis, irritable bowel syndrome, and Crohn's disease, are widespread. In the US, gastrointestinal disorders are estimated to affect 60 to 70 million people annually. For some disorders, early screening and diagnosis has resulted in a reduction in mortality rates and improved quality of life for patients. However, standard methods of diagnosis, such as colonoscopy, are invasive, time-consuming, and are associated with relatively high costs. There is a continuing need for noninvasive methods of diagnosing gastrointestinal disorders in both humans and animals.

SUMMARY

Provided herein are methods of detecting colorectal neoplasia in a subject, the method comprising measuring the level of expression of 2, 3, 4, 5, 6, 7, 8, 9, 10, 11, 12, 13, 14, 15, 16, 17, 18, 19, 20, 21, 22, 23, 24, 25, 26, 27, 28 or 29 stool-derived eukaryotic RNA biomarkers selected from the biomarkers listed in Table 1 or Table 2 or a combination of Table 1 and Table 2 in eukaryotic nucleic acid extracted from a stool sample from the subject; comparing the measured expression level of the 2, 3, 4, 5, 6, 7, 8, 9, 10, 11, 12, 13, 14, 15, 16, 17, 18, 19, 20, 21, 22, 23, 24, 25, 26, 27, 28 or 29 stool-derived eukaryotic RNA biomarkers in the stool sample with the measured expression level of the 2, 3, 4, 5, 6, 7, 8, 9, 10, 11, 12, 13, 14, 15, 16, 17, 18, 19, 20, 21, 22, 23, 24, 25, 26, 27, 28, or 29 stool-derived eukaryotic RNA biomarkers in a control, wherein a difference in the measured expression level of the 2, 3, 4, 5, 6, 7, 8, 9, 10, 11, 12, 13, 14, 15, 16, 17, 18, 19, 20, 21, 22, 23, 24, 25, 26, 27, 28 or 29 stool-derived eukaryotic RNA biomarkers in the stool sample relative to the measured expression level of the 2, 3, 4, 5, 6, 7, 8, 9, 10, 11, 12, 13, 14, 15, 16, 17, 18, 19, 20, 21, 22, 23, 24, 25, 26, 27, 28 or 29 stool-derived eukaryotic RNA biomarkers in the control indicates that the subject has colorectal neoplasia. Also provided is a method of detecting colorectal neoplasia in a subject, the method comprising: measuring the variant allele frequency of one or more variant biomarker genes selected from the biomarker genes listed in Table 3 in eukaryotic nucleic acid extracted from a stool sample from the subject; comparing the measured variant allele frequency of the one or more variant biomarker genes in the stool sample with the measured variant allele frequency of the one or more variant biomarker genes in a control, wherein a difference in the variant allele frequency of the one or more variant biomarker genes relative to the variant allele frequency of the one or more variant biomarker genes in the control indicates that the subject has or is at risk for colorectal cancer. Also provided is a method of detecting a molecular subtype of colorectal cancer in a subject, the method comprising: measuring the level of expression of two or more biomarker genes selected from any of the colorectal neoplasm molecular subtype biomarker genes listed in Table 4 in eukaryotic nucleic acid extracted from a stool sample from the subject; comparing the measured expression level of the two or more colorectal neoplasm molecular subtype biomarker genes in the biological sample with the measured expression level of the two or more colorectal neoplasm molecular subtype biomarker genes in a control, wherein a difference in the measured expression level of the two or more colorectal neoplasm molecular subtype biomarker genes in the biological sample with the measured expression level of the two or more colorectal neoplasm molecular subtype biomarker genes relative to the two or more colorectal neoplasm molecular subtype biomarker genes in the control indicates the molecular subtype of colorectal cancer.

BRIEF DESCRIPTION OF THE DRAWINGS

These and other features and advantages of the present invention will be more fully disclosed in, or rendered obvious by, the following detailed description of the preferred embodiment of the invention, which is to be considered together with the accompanying drawings wherein like numbers refer to like parts and further wherein:

FIG. 1A is an electrophoresis file run. The electrophoretic analysis was used to check the quality of the RNA extracted based on a method described in the literature.

FIG. 1B is an electrophoresis file run. The electrophoretic analysis was used to check the quality of the RNA extracted based on a method described herein.

FIG. 2A is an electrophoresis file run. The electrophoretic analysis was used to check the quality of seRNA for samples that were extracted immediately, without incubation in a stabilization buffer.

FIG. 2B is an electrophoresis file run. The electrophoretic analysis was used to check the quality of seRNA for samples that were incubated in a stabilization buffer and stored at room temperature for 24 hours prior to extraction.

FIG. 2C is an electrophoresis file run. The electrophoretic analysis was used to check the quality of seRNA for samples that were incubated in a stabilization buffer and stored at room temperature for 48 hours prior to extraction.

FIG. 4A is a table listing the 274 colorectal neoplasm molecular subtype biomarker genes employed in the Colorectal Cancer Subtyping Consortium classifier.

FIG. 4B is a table listing the 25 exemplary colorectal neoplasm molecular subtype biomarker genes useful for identification of colorectal cancer subtype CMS1.

FIG. 9 is a table listing biomarkers relating to cancer, colorectal neoplasms, and/or gastrointestinal health where putative somatic variants could be identified.

FIG. 10 is a table summarizing patient demographics and processing metrics associated with the prospective training set, the prospective hold out test set, the retrospective hold out test set, and the whole study cohort.

FIG. 14 is a table with features ranked by Gini Importance.

FIG. 15A is a graph showing model performance for detection of HRAs based on the independent hold out test set (n=110 patients) without the fecal immunochemical test (FIT) feature.

FIG. 15B is a graph showing model performance for detection of HRAs based on the independent hold out test set (n=110 patients) with the fecal immunochemical test (FIT) feature.

DETAILED DESCRIPTION

Figures 3A, 3B:
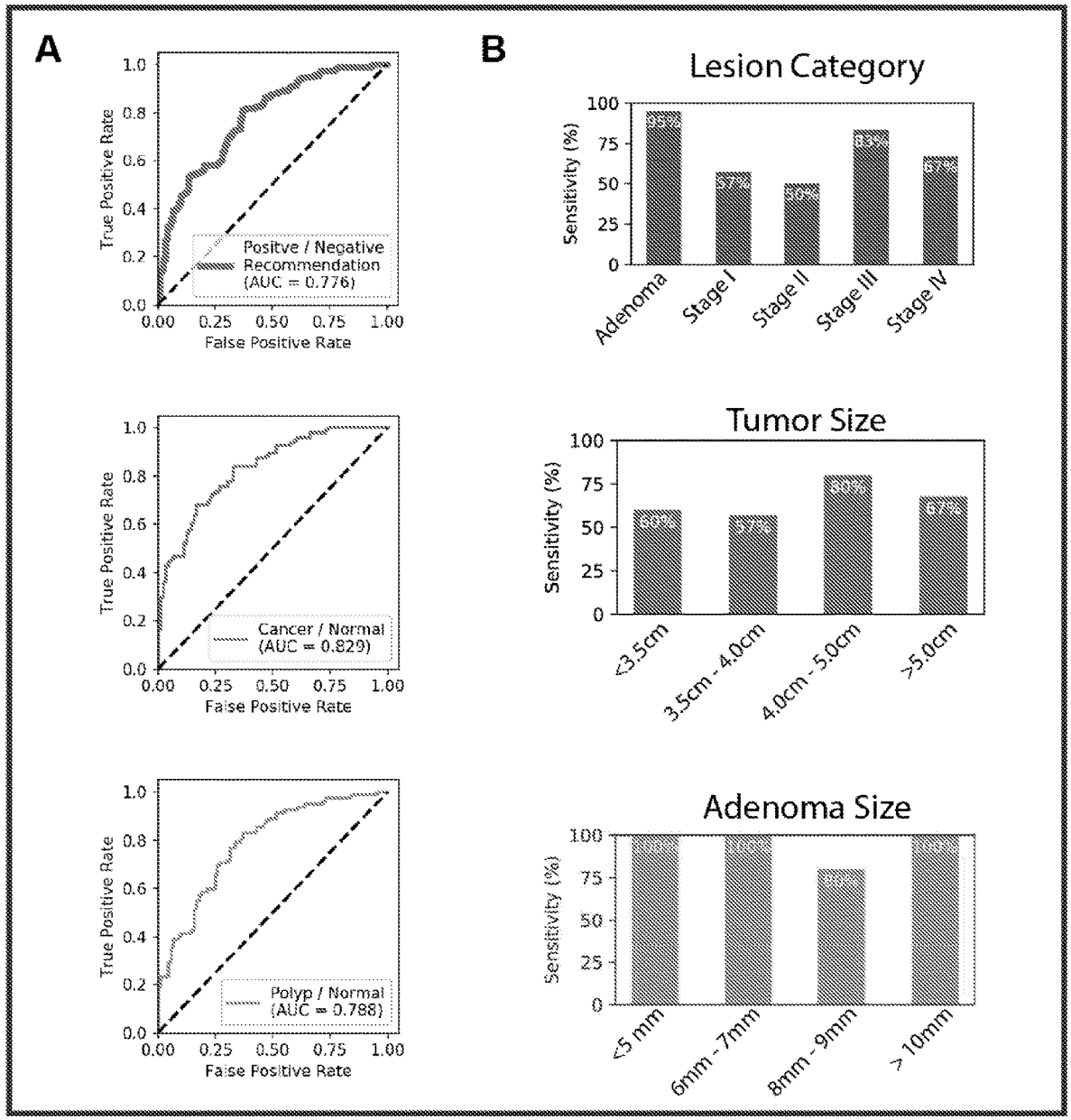
FIG. 3A depicts ROC analyses for various patient populations attained during internal validation of an SVM.
FIG. 3B depicts sensitivity of prediction for an SVM employed on an independent test set.

This description of preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship. When only a single machine is illustrated, the term "machine" shall also be taken to include any collection of machines that individually or jointly execute a set (or multiple sets) of instructions to perform any one or more of the methodologies discussed herein. In the claims, means-plus-function clauses, if used, are intended to cover the structures described, suggested, or rendered obvious by the written description or drawings for performing the recited function, including not only structural equivalents but also equivalent structures.

The present invention is based in part on the inventors' development of a method to separate eukaryotic cells from bacterial cells in a stool sample, for example, a stool sample obtained from a mammal. Within the colon, there are about approximately $1 \times 10^{13}$ bacterial cells per gram of intestinal content. This colonic microflora can include between 300-1000 species. A stool or fecal sample is a complex macromolecular mixture that includes not only eukaryotic cells sloughed off from the intestinal lumen of the gastrointestinal tract, but microbes, including bacteria and any gastrointestinal parasites, indigestible unabsorbed food residues, secretions from intestinal cells, and excreted material such as mucous and pigments. Normal stool is made up of about 75% water and 25% solid matter. Bacteria make up about 60% of the total dry mass of feces. The high bacterial load can contribute to an unfavorable signal-to-noise ratio for the detection of eukaryotic biomarkers from a stool sample. Furthermore, the eukaryotic signals can be heavily degraded. Extraction and processing of such eukaryotic nucleic acids can promote or accelerate degradation, which severely limits further analysis.

The extraction method permits the isolation of high-quality eukaryotic RNA from a stool sample. The methods are described in International Application WO2018/081580, which is herein incorporated by reference in its entirety. We may refer to stool-derived eukaryotic RNA (seRNA) to specify the eukaryotic RNA preserved during the process of fecal matter generation, and which is subsequently extracted from stool samples by the method disclosed in International Application WO2018/081580.

Thus, the inventors developed materials and methods for noninvasively assessing the transcriptome of human colorectal cancers and colorectal neoplasia. The materials and methods disclosed herein provide efficient and sensitive detection of eukaryotic nucleic acids in a human stool sample. The inventors have found that they could detect colorectal neoplasms based on the expression levels and variants of stool-derived eukaryotic RNA biomarkers in eukaryotic nucleic acid present in a stool sample from the subject. The detection methods can be configured in ways that are useful for detecting various forms and subtypes of colorectal cancers or colorectal neoplasia.

More specifically, the materials and methods disclosed herein can be used to detect high-risk adenomas (HRAs) based on the expression levels of stool-derived eukaryotic RNA biomarkers in eukaryotic nucleic acid present in a stool sample from the subject. Disclosed herein is a model-based approach for prediction or identification of colorectal neoplasms, and specifically, high-risk adenomas. In some embodiments, the model can be based on the expression level of two or more stool-derived eukaryotic RNA biomarkers listed in Table 1 and Table 2 in eukaryotic nucleic acid present in a stool sample from the subject. In some embodiments, the model can be based on the expression level of two or more stool-derived eukaryotic RNA biomarkers, for example, 2, 3, 4, 5, 6, 7, 8, 9, 10, 11, 12, 13, 14, 15, 16, 17, 18, 19, 20, 21, 22, 23, 24, 25, 26, 27, 28, or 29 of the stool-derived eukaryotic RNA biomarkers selected from the stool-derived eukaryotic RNA biomarkers listed in Table 1 or Table 2 or a combination of Table 1 and Table 2. In some embodiments, the model can be based on expression level of two or more stool-derived eukaryotic RNA biomarkers, for example 2, 3, 4, 5, 6, 7, 8, 9, 10, or 11 of the stool-derived eukaryotic RNA biomarkers listed in Table 1. The model can also include demographic features, for example, the subject's age and smoking status. In some embodiments, the model can also include the results of a fecal immunochemical test (FIT) administered to a stool sample from the subject. In some embodiments, the materials and methods disclosed herein can be used to identify medium-risk adenomas (MRAs), low-risk adenomas (LRAs), or benign polyps.

Also provided are materials and methods for detecting colorectal cancer based on the detection of a variant biomarker in a eukaryotic nucleic acid in a stool sample from a subject. In some embodiments the variant biomarker can be associated with colorectal cancer tumorigenesis. The variant can be a variant of any of the biomarkers listed in Table 3. A variant can be a variant in a colorectal cancer driver gene, for example, TP53, KRAS, PIK3CA, BRAF, APC, BMP3, NDRG4, SMAD4, MLH1, CTNNB1, EGFR, BRCA1, CDKN2A, CDH1, PTEN, VEGFA, MAPK3, or NRAS.

The inventors have found that they could effectively detect gene expression signatures associated with the consensus molecular subtypes (CMS) as defined by the Colorectal Cancer Subtyping Consortium (CRCSC) in stool-derived eukaryotic RNA. More specifically, the materials and methods disclosed herein could be used to isolate seRNA from stool samples that can indicate the presence of a particular subtype of colorectal cancer (e.g. CMS1), as defined by the CRCSC. Of individuals diagnosed with colorectal cancer, approximately 14% have CMS1 classification. CMS1 tumors are characterized by increased microsatellite instability (MSI-H), hypermutation, and immune infiltrate. These features are consistent with tumors in which the immune system plays an active role in detecting and surveying the tumor site. Patients having such tumors may benefit from targeted immunotherapy such as immune checkpoint blockade therapy. For example, both Keytruda™ (pembrolizumab) and Opdivo™ (nivolumab) have been approved by the FDA for the treatment of adult and pediatric patients with unresectable or metastatic solid tumors that are MSI-H and do not benefit from first-line chemotherapy.

Thus, provided herein are materials and methods for determining whether a human subject with colorectal cancer has gene expression signatures associated with CMS1. In the context of disease monitoring, the method can noninvasively and selectively identify this patient population and provide treatment guidance using seRNA. The methods can be performed efficiently and noninvasively using a stool sample rather than a blood or biopsy sample. The methods are useful in the development of a clinical plan and method of treatment for a subject having colorectal cancer or who is at risk for colorectal cancer. In some embodiments, the two or more biomarkers can include combinations of 2, 3, 4, 5, 6, 7, 8, 9, 10, 11, 12, 13, 14, 15, 16, 17, 18, 19, 20, 21, 22, 23, 24, 25, 30, 35, 40, 45, 50, 60, 70, 80, 90, 100, 120, 140, 160, 180 or more of the markers in FIGS. 4A-4B or Table 4. In some embodiments, the markers can be contained within differentially expressed transcript clusters and/or common pathways associated with colorectal cancer. Exemplary pathways include microsatellite instability (MSI), chromosomal instability (CIN), and CpG island methylator phenotype (CIMP). In some embodiments, the pathways can be cellular components pathways, cellular response to stress, stress, and RNA binding pathways.

In the context of disease monitoring, the method can noninvasively and selectively identify a patient population and provide treatment guidance. The methods can be performed efficiently and noninvasively using a stool sample rather than a blood or biopsy sample. The methods are useful in the development of a clinical plan and method of treatment for a subject having colorectal neoplasms or colorectal cancer or who is at risk for colorectal neoplasms or colorectal cancer.

The methods and materials disclosed herein include methods for isolating eukaryotic nucleic acids from a stool sample. Such eukaryotic nucleic acids can be evaluated for levels of specific biomarkers that may be indicative of a gastrointestinal disorder or disease, for example, a colorectal neoplasm or colorectal cancer, in a eukaryote, for example, a mammal. The mammal can be a human or a non-human animal, for example, a human, dog, cat, non-human primate, ruminant, ursid, equid, pig, sheep, goat, camelid, buffalo, deer, elk, moose, mustelid, rabbit, guinea pig, hamster, rat, mouse, pachyderm, rhinoceros, or chinchilla.

The inventors have found that that they could effectively separate eukaryotic cells from bacterial cells in a eukaryotic stool sample. The inventors have also found that they could detect eukaryotic biomarkers in the RNA isolated from such eukaryotic cells. Such biomarkers may be useful for the detection of gastrointestinal disorders, for example, colorectal cancer, celiac disease, Crohn's disease, ulcerative colitis, gastritis, gastroenteritis, gastric cancer, gastric ulcers, necrotizing enterocolitis, gastrointestinal stromal tumors, gastrointestinal lymphoma, gastrointestinal neoplasia, lymphosarcoma, adenoma, hyperplastic change, adenocarcinoma, inflammatory bowel disease, irritable bowel syndrome, pancreatic neoplasia, hepatic neoplasia, cholangiocarcinoma, colitis. Provided herein are materials and methods for determining whether a subject, for example, a human, a dog, or a cat, is at risk for gastrointestinal disease, for example, a colorectal neoplasm, for example, a high-risk adenoma or colorectal cancer. Also provided are materials and methods for diagnosis of disease and methods of identifying the health status of a subject.

The methods and compositions disclosed herein are generally and variously useful for the detection, diagnosis, classification, and treatment of gastrointestinal disorders, for example a colorectal neoplasm or colorectal cancer. Methods of detection can include measuring the expression level in a stool sample of one, two, or more biomarkers in a sample from a subject, for example, a patient, having a gastrointestinal disorder or suspected of having a gastrointestinal disorder and comparing the measured expression level to the measured expression level of one, two, or more biomarkers in a control. A difference in the measured expression level of one, two, or more biomarkers in a subject's sample relative to the measured expression level of the one, two, or more biomarkers in a control is an indication that the subject has a gastrointestinal disorder. In some embodiments, a difference in the measured expression level of one, two, or more biomarkers in a subject's sample relative to the measured expression level of the one, two, or more biomarkers in a control is an indication that the subject, for example, a patient, is at risk for a gastrointestinal disorder.

In some embodiments, methods of detection can include measuring the expression level in a stool sample of 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers in a sample from a subject, for example, a patient, having a gastrointestinal disorder, for example, a colorectal neoplasm, or suspected of having a gastrointestinal disorder, for example, a colorectal neoplasm, and comparing the measured expression level to the measured expression level of the 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers in a control. A difference in the measured expression level of the 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers in a subject's sample relative to the measured expression level of the 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers in a control is an indication that the subject has a gastrointestinal disorder, for example, a colorectal neoplasm. In some embodiments, a difference in the measured expression level of the 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers in a subject's sample relative to the measured expression level of the 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers in a control is an indication that the subject, for example, a patient, is at risk for a gastrointestinal disorder, for example, a colorectal neoplasm. In some embodiments, a difference in the measured expression level of the 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers in a subject's sample relative to the measured expression level of the 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers in a control is an indication that the subject, for example, a patient, is at risk for a particular type of colorectal neoplasia, for example, an adenoma, and more specifically, a high-risk adenoma. In any of the preceding embodiments, the stool-derived eukaryotic RNA biomarkers can be selected from the stool-derived eukaryotic RNA biomarkers listed in Table 1 or Table 2 or a combination of Table 1 and Table 2. Methods of detection can also include an analysis of variants of specific biomarkers.

In another embodiment, methods of detection of disease can include measuring the relative expression level proportion, for example, the relative ratios, of 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers in a subject's stool sample and comparing the relative proportion of these stool-derived eukaryotic RNA biomarkers to the relative expression level proportion of the 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers in a control. A difference in the measured relative expression level proportion of the 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers in a subject's sample relative to a control is an indication that the subject has a gastrointestinal disease, for example, a colorectal neoplasm. In some embodiments, a difference in the measured expression level proportion of the 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers in a subject's sample relative to the measured expression level proportion of the 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers in a control is an indication that the subject is at risk for a gastrointestinal disorder, for example, a colorectal neoplasm. In some embodiments, a difference in the measured expression level proportion of the 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers in a subject's sample relative to the measured expression level proportion of the 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers in a control is an indication that the subject is at risk for a particular type of colorectal neoplasia, for example, an adenoma, and more specifically, a high-risk adenoma. In any of the preceding embodiments, the stool-derived eukaryotic RNA biomarkers can be selected from the stool-derived eukaryotic RNA biomarkers listed in Table 1 or Table 2 or a combination of Table 1 and Table 2. Methods of detection can also include an analysis of variants of specific biomarkers.

The methods can include determining the level of expression of 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers in eukaryotic RNA isolated from a stool sample obtained from a subject by determining whether the levels of the 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers are different relative to the levels of the same 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers in a control. Exemplary stool-derived eukaryotic RNA biomarkers are listed in Table 1 and Table 2. Exemplary stool-derived eukaryotic RNA biomarkers can include ACY1, TNFRSF10B, DST, EGLN2, PER3, CTNNB1, ACHE, SMAD4, EDN1, ERBB2, GAPDH. ABCB1, MAPK3, VEZF1, KRAS, PTEN, CREBBP, SUZ12, CDHRS, CABLES1 AREG, SPATA2, PPARGC1A, DBP, CDH1, PDGFA, OGG1, CGN, and TCF7L2.

TABLE 1

Stool-derived eukaryotic RNA biomarkers

| Biomarker | Exemplary Genbank Entry |
|---|---|
| ACY1 | NM_000666.3 |
| TNFRSF10B | NM_003842.5 |
| DST | XM_011514826.3 |
| EGLN2 | NM_080732.4 |
| PER3 | XM_024450585.1 |
| CTNNB1 | NM_001904.4 |
| ACHE | KJ425573.1 |
| SMAD4 | NM_005359.5 |
| EDN1 | NM_001955.5 |
| ERBB2 | XM_024450643.1 |
| GAPDH | NM_002046.7 |

TABLE 2

Stool-derived eukaryotic RNA biomarkers

| Biomarker | Exemplary Genbank entry |
|---|---|
| ABCB1 | AF399931.1 |
| MAPK3 | BC013992.1 |
| VEZF1 | NM_007146.3 |
| KRAS | M54968.1 |
| PTEN | KX398936.1 |
| CREBBP | U85962.3 |
| SUZ12 | NM_015355.4 |
| CDHR5 | NM_021924.4 |
| CABLES1 | EF028204.1 |
| AREG | NM_001657.4 |
| SPATA2 | BC009481.2 |
| PPARGC1A | HQ695733.1 |
| DBP | NM_001352.4 |
| CDH1 | NM_004360.5 |
| PDGFA | M22734.1 |
| OGG1 | AF003595.1 |
| CGN | NM_020770.3 |
| TCF7L2 | CR536574.1 |

In some embodiments, the stool-derived eukaryotic RNA biomarkers can also include subsets of stool-derived eukaryotic RNA biomarkers listed in Table 1 and Table 2. Some or all of the stool-derived eukaryotic RNA biomarkers listed in Table 1 or Table 2 or a combination of Table 1 and Table 2 can form a panel. For example, some or all of the stool-derived eukaryotic RNA biomarkers in Table 1 can form a panel (Panel A). For example, Panel A can include some or all of the stool-derived eukaryotic RNA biomarkers ACY1, TNFRSF10B, DST, EGLN2, PER3, CTNNB1, ACHE, SMAD4, EDN1, ERBB2, GAPDH. The compositions can include gene arrays and probe sets configured for the specific detection of the panels of markers disclosed herein. The compositions can also include kits comprising gene arrays and probe sets configured for the specific detection of the panels of markers disclosed herein. The methods can include identifying the presence of a variant in the nucleic acid sequence of a stool-derived eukaryotic RNA biomarker, for example, the stool-derived eukaryotic RNA biomarkers listed in Table 1 and Table 2.

Also provided are methods of detection of a variant in the nucleic acid sequence of a biomarker in a eukaryotic nucleic acid (e.g., seRNA). A variant can be any mutation that contributes to tumor survival, tumor progression, or tumor metastasis. We may refer to such mutations as "driver mutations" or "progressor mutations." Such mutations can include silent mutations, missense mutations, insertions, deletions, frameshift mutations or nonsense mutations. The expression of any particular variant can also be described as the "variant allele frequency" (VAF). Such variants can include variants in any of the biomarkers listed in FIG. 8, or 9. A variant can be a variant in a colorectal cancer driver gene, for example, TP53, KRAS, PIK3CA, BRAF, APC, BMP3, NDRG4, SMAD4, MLH1, CTNNB1, EGFR, BRCA1, CDKN2A, CDH1, PTEN, VEGFA, MAKP3, or NRAS. Exemplary stool-derived eukaryotic RNA variant biomarkers are listed in Table 3.

TABLE 3

Stool derived eukaryotic RNA biomarkers and variants

| Biomarker | Exemplary Genbank Entry | Exemplary Variant |
|---|---|---|
| APC | M74088.1 | chr5: 112175639 C > T p.R1450* NM_000038 c.C4348T |
| KRAS | M54968.1 | chr12: 25398284 C > T p.G12D NM_033360 c.G35A |
| TP53 | KX710182.1 | chr17: 7577538 C > T p.R248Q NM_000546 c.G743A |
| BMP3 | NM_001201.4 | chr4: 81967371 C > T p.P266S NM_001201 c.C796T |
| NDRG4 | BC011795.2 | chr16: 58538324 G > A p.G136R NM_020465 c.G406A |
| SMAD4 | NM_005359.5 | chr18: 48591919 G > A p.R361H NM_005359 c.G1082A |
| MLH1 | U07343.1 | chr3: 37067240 T > A p.V384D NM_000249 c.T1151A |
| CTNNB1 | NM_001904.4 | chr3: 41266137 C > T p.S45S NM_001904 c.C134T |
| EGFR | NM_005228.5 | chr7: 55228007 p.S492R NM_005228 c.A1474C |
| BRCA1 | U14680.1 | chr17: 41243770 A > C p.L1260V NM_007294 c.T3778G |
| CDKN2A | JQ694045.1 | chr9: 2197112 G > A p.R80* NM_000077 c.C238T |
| CDH1 | NM_004360.5 | chr16: 68849598 G > A p.V501M NM_004360 c.G1501A |
| PIK3CA | NM_006218.4 | chr3: 178936091 G > A p.E545K NM_006218 c.G1633A |
| PTEN | KX398936.1 | chr10: 89692905 G > A p.R130Q NM_000314 c.G389A |
| VEGFA | NM_001171623.1 | chr6: 43745357 G > T p.E90D NM_001171623 c.G270T |
| BRAF | M95712.2 | chr7: 140453136 A > T p.V600E NM_004333 c.T1799A |
| MAPK3 | BC013992.1 | chr16: 30128482 G > C p.D300E NM_002746 c.C900G |
| NRAS | AF493919.1 | chr1: 115256530 G > T p.Q61K NM_002524 c.C181A |

The methods can include identifying the presence of a variant in the nucleic acid sequence of a biomarker, for example the biomarkers listed in Table 3. Some or all of the colorectal neoplasm biomarker genes listed in Table 3 can form a panel (Panel B). In some embodiments, the colorectal neoplasm biomarker genes listed in Table 3 can also include subsets of colorectal neoplasm subtype biomarkers. The compositions can include gene arrays and probe sets configured for the specific detection of the panels of markers disclosed herein. The compositions can also include kits comprising gene arrays and probe sets configured for the specific detection of the panels of markers disclosed herein.

In another embodiment, methods of detection of disease can include measuring the relative variant allele frequency, for example, the relative ratios, of one, two, or more variants in any of the biomarker genes listed in Table 3 in a subject's stool sample and comparing the relative variant allele frequency of these biomarkers to the variant allele frequency of one, two, or more biomarkers in a control. A difference in the measured variant allele frequency of one, two, or more biomarkers in a subject's sample relative to the measured variant allele frequency in a control is an indication that the subject has a gastrointestinal disease. In some embodiments, a difference in the variant allele frequency of the one, two, or more biomarkers in a subject's sample relative to the measured variant allele frequency of the one, two, or more biomarkers in a control is an indication that the subject is at risk for a gastrointestinal disorder.

Also provided are methods of detection of colorectal neoplasm molecular subtype biomarkers. Colorectal cancer can be classified into four different molecular subtypes based on expression of particular markers. The four consensus molecular subtypes (CMS1-4) are predicted based upon the expression of 274 genes (based upon their unique HUGO gene name identifiers), depicted in FIG. 4A. The random forest classifier, described by the CRCSC, uses the expression of the 274 genes as features to accurately identify the molecular subtype classification. The four CMS subtypes include CMS1-4. CMS1 is associated with hypermutation and microsatellite instability. CMS1 tumors typically have an immune infiltrate. CMS1 tumors tend to have higher histopathological grade at diagnosis and are associated with poor survival. CMS2 also referred to as the "canonical" subtype, are epithelial tumors characterized by marked WNT and MYC signaling activation, and increased copy number alterations and tend to be associated with long-term survival. CMS3 are epithelial tumors characterized by evident metabolic dysregulation, and mutations in KRAS, receptor tyrosine kinases, and the MAPK pathway. CMS4 tumors are mesenchymal tumors characterized by transforming growth factor-13 activation, stromal invasion and angiogenesis. CMS4 tumors tend to be diagnosed at advanced stages (stages III and IV) and are correlated with poorer overall survival rates and poorer relapse free survival. Twenty-five genes (based upon their unique HUGO gene name identifiers) that are particularly influential in the prediction of CMS1 are depicted in FIG. 4B and Table 4.

TABLE 4

Stool-derived eukaryotic RNA biomarkers for the CMS1 colorectal cancer subtype

| Biomarker | Exemplary Genbank Entry |
| --- | --- |
| QPRT | BC010033.2 |
| RNF43 | BC109028.2 |
| TFAP2A | BC017754.1 |
| TSPAN6 | BC012389.1 |
| TRIM7 | AF220032.1 |
| GNLY | BC023576.2 |
| AXIN2 | AF205888.1 |
| FITM2 | NM_001080472.4 |
| GNG4 | AF493872.1 |
| VAV3 | AF067817.1 |
| RETNLB | NM_032579.2 |
| DUSP4 | BC002671.2 |

TABLE 4-continued

Stool-derived eukaryotic RNA biomarkers for the CMS1 colorectal cancer subtype

| Biomarker | Exemplary Genbank Entry |
| --- | --- |
| TNFAIP6 | NM_007115.4 |
| HOXC6 | CR456954.1 |
| TRIB2 | NM_021643.3 |
| CEL | NM_001807.5 |
| GPR143 | NM_000273.3 |
| ASCL2 | NM_005170.2 |
| SLC5A6 | BC015631.2 |
| GAS1 | NM_002048.3 |
| B3GNT6 | NM_138706.5 |
| CYP2B6 | AF182277.1 |
| BCAT1 | NM_005504.7 |
| FAP | NM_004460.5 |
| BOC | AY358328.1 |

The methods can include determining the level of expression of two or more colorectal neoplasm subtype biomarkers in the human RNA isolated from a stool sample obtained from a subject by determining whether the levels of the two or more colorectal neoplasm subtype biomarker genes in the stool sample from a subject are different relative to the levels of the same two or more colorectal neoplasm subtype biomarker genes in a control. Exemplary colorectal neoplasm subtype biomarker genes are shown in Table 4. Some or all of the colorectal neoplasm biomarker genes listed in Table 4 can form a panel (Panel C). In some embodiments, the colorectal neoplasm biomarker genes listed in Table 4 can also include subsets of colorectal neoplasm subtype biomarkers. The compositions can include gene arrays and probe sets configured for the specific detection of the panels of markers disclosed herein. The compositions can also include kits comprising gene arrays and probe sets configured for the specific detection of the panels of markers disclosed herein.

In another embodiment, methods of detection of disease can include measuring the relative expression level proportion, for example, the relative ratios, of one, two, or more two or more colorectal neoplasm subtype biomarkers in a subject's stool sample and comparing the relative proportion of these biomarkers to the relative expression level proportion of one, two, or more biomarkers in a control. A difference in the measured relative expression level proportion of one, two, or more biomarkers in a subject's sample relative to a control can indicate the molecular subtype of colorectal cancer. In some embodiments, a difference in the measured expression level proportion of the one, two, or more biomarkers in a subject's sample relative to the measured expression level proportion of the one, two, or more biomarkers in a control is an indication that the subject may develop a particular subtype of colorectal cancer.

Alternative methods to detect CMS1 tumors, also referred to as MSI-H tumors, can be used. Genomic variants in POLE, MLH1, MSH2, MSH6, and PMS2 implicated in DNA mismatch repair deficiencies have been used as predictive biomarkers in clinical trials for immune checkpoint blockade therapies. Gene expression profiles focused on expression of immune inhibitory molecules, including PD-1, PD-L1, CTLA-4, LAG-3, and IDO, can further be used to predict the increased immunogenicity of the microenvironment of MSI-H tumors and further predict the eligibility of a patient to benefit from checkpoint immunotherapy.

Provided herein are stool-derived eukaryotic RNA biomarkers and panels of stool-derived eukaryotic RNA biomarkers for use in diagnosis of colorectal neoplasms or a particular subtype precancerous lesion or colorectal cancer. A biomarker is generally a characteristic that can be objectively measured and quantified and used to evaluate a biological process, for example, colorectal neoplasm development, progression, remission, or recurrence. Biomarkers can take many forms including, nucleic acids, polypeptides, metabolites, or physical or physiological parameters.

In general, biomarkers from eukaryotic cells can include: a) a sequence of deoxyribonucleic acid (DNA), b) a sequence of ribonucleic acid (RNA), c) a predicted sequence of amino acids, which comprise the backbone of protein, d) expression levels of ribonucleic acid biomarkers, e) a predicted expression level of an amino acid sequence or f) any combination of the above. In some embodiments, a biomarker can be a fragment of a larger sequence, for example, a fragment of a longer RNA sequence, a longer DNA sequence or a longer polypeptide sequence. In some embodiments, biomarkers, such as GAPDH, ACTB or others, can be used for normalization of other biomarkers. In other embodiments, features, such as total RNA counts, total RNA input or others, can be used as biomarkers or for normalization of other biomarkers.

Stool-derived eukaryotic RNA biomarkers can be quantified using amplicons. Amplicons can contain zero, one, two, or more unique sequences. Amplicons for the same stool-derived eukaryotic RNA biomarker can vary in percent sequence identity. Amplicons can be designed to target different loci. Targeted loci can include: a) geographically similar loci on the same transcript from the same gene, b) geographically unique loci on the same transcript from the same gene, c) geographically unique loci on different transcripts from the same gene, or d) geographically unique loci on different transcripts from different genes. In some embodiments, amplicons designed to target different loci can reflect structural features of a particular RNA, for example, sequence or secondary structure that might either be protected or preferentially degraded in stool. In some embodiments, amplicons designed to target different loci can reflect specific disease parameters, for example, in diseases in which specific alternatively spliced transcripts are increased or decreased.

A biological sample can be a sample that contains cells or other cellular material from which nucleic acids or other analytes can be obtained. A biological sample can be a control or an experimental sample. A biological sample can be a stool sample. The biological sample can be obtained immediately following defecation in a toilet, on the ground, into a litter box, or into a collection device. In some embodiments, the biological sample can be obtained following or during a procedure, such as an enema, a fecal swab, or an endoscopy. The biological sample can be tested immediately. Alternatively, the biological sample can be stored in a buffer prior to testing, for example an aqueous buffer, a glycerol-based buffer, a polar solvent based buffer, an osmotic balance buffer, or other buffer sufficient for preserving the biological sample. Additionally, or alternatively, the biological sample can be collected and stored refrigerated, for example, at 4° C., or frozen, for example, at 0° C., −20° C., −80° C., −140° C., or lower prior to testing. The biological sample can be stored for 1 month, 2 months, 4 months, 6 months, 1 year, 2 years or more prior to testing.

The biological sample can be derived from a eukaryote, for example a mammal. The mammal can be a human or a non-human animal, for example, a human, dog, cat, non-human primate, ruminant, ursid, equid, pig, sheep, goat, camelid, buffalo, deer, elk, moose, mustelid, rabbit, guinea pig, hamster, rat, mouse, pachyderm, rhinoceros, or chinchilla. Thus, a stool sample can be obtained from a human or a non-human animal, for example, a human, dog, cat, non-human primate, ruminant, ursid, equid, pig, sheep, goat, camelid, buffalo, deer, elk, moose, mustelid, rabbit, guinea pig, hamster, rat, mouse, pachyderm, rhinoceros, or chinchilla.

Useful methods for isolation of nucleic acids from a biological sample, for example a stool sample, that are enriched for eukaryotic nucleic acids are provided herein. The methods can include disrupting the stool sample with buffer. The sample can be subjected to vortexing, shaking, stirring, rotation, or other methods of agitation sufficient to disperse the solids and the stool bacteria. The temperature at which the agitation and centrifugation steps are carried out can vary, for example, from about 4° C. to about 20° C., from about 4° C. to about 1° C., from about 4° C. to about 10° C., from about 4° C. to about 6° C. Following disruption, the sample can be subjected to one or more rounds of centrifugation. In some embodiments, the disruption step and the centrifugation step can be repeated one, two, three, or more additional times. Commercially available reagents, for example Nuclisens® EasyMag® reagents can be used for stool disruption, washing, and cell lysis. Lysis buffer can also be used to lyse the eukaryotic cells. The lysate can be further centrifuged at any temperature for any duration of time for any number of times. After centrifugation, the supernatant can be used as input into an automated RNA isolation machine, for example an EasyMag® instrument. In some embodiments, the extracted nucleic acids can be treated with DNase to degrade DNA in the solution. Other methods of RNA purification can be used; for example, following mechanical or enzymatic cell disruption, a solid phase method can be performed such as column chromatography or extraction with organic solvents, for example, phenol-chloroform or thiocyanate-phenol-chloroform extraction. In some embodiments, the nucleic acids can be extracted onto a functionalized bead. In some embodiments, the functionalized bead can further comprise a magnetic core ("magnetic bead"). In some embodiments, the functionalized bead can include a surface functionalized with a charged moiety. The charged moiety can be selected from: amine, carboxylic acid, carboxylate, quaternary amine, sulfate, sulfonate, or phosphate.

For extraction of nucleic acids, the stool sample can be disrupted in the presence of one or more of a buffer, a surfactant, and a ribonuclease inhibitor to form a suspension. The buffer can be a biologically compatible buffer, for example, Hanks balanced salt solution, Alsever's solution, Earle's balanced salt solution, Gey's balanced salt solution, Phosphate buffered saline, Puck's balanced salt solution, Ringer's balanced salt solution, Simm's balanced salt solution, TRIS-buffered saline, or Tyrode's balanced salt solution. The surfactant can be an ionic or non-ionic surfactant, for example, Tween-20, or Triton-X-100. The ribonuclease inhibitor can be solvent based, protein based, or another type of method to prevent RNA destruction, including, for example, Protector RNase Inhibitor (Roche), RNasin® (Promega), SUPERase-In™ (Thermo Fisher Scientific), RNase-OUT™ (Thermo Fisher Scientific), ANTI-RNase, Recombinant RNase Inhibitor, or a cloned RNase Inhibitor. The stool sample can be disrupted in a variety of ways, for example by vortexing, shaking, stirring, rotating, or other method of agitation sufficient to disperse the solids and the stool bacteria. In some embodiments, the stool sample can be disrupted using: coated beads, magnetic beads, or a stirring implement, such as a glass rod, a metal rod, a wooden stick, or a wooden blade.

The suspension can then be separated into a liquid portion and a solid portion. The separation can be carried out, for example, by centrifugation, filtration, targeted probes that specifically bind eukaryotic cells, antibodies, column-based filtration, bead-based filtration, or chromatographic methods. The liquid portion is enriched for bacterial nucleic acids and can be discarded. The solid portion can be re-suspended in a buffer either in the presence or absence of a surfactant and in the presence or absence of a ribonuclease. The separation step can be repeated one, two, three, four, five, six, seven, eight, or more times.

The temperature at which the disruption and separation steps are carried out can vary, for example, from about 4° C. to about 20° C., from about 4° C. to about 15° C., from about 4° C. to about 10° C., from about 4° C. to about 6° C.

The resulting pellet obtained from the separation step can be suspended in a lysis buffer, for example, a buffer comprising a chaotropic agent and optionally a surfactant to form a lysate. In some embodiments, the chaotropic agent can be guanidium thiocyanate and the surfactant can be Triton-X-100. In some embodiments, the lysis buffer can include or exclude Tris-HCl, ethylenediaminetetraacetic acid (EDTA), sodium dodecyl sulfate (SDS), Nonidet P-40, sodium deoxycholate, or dithiothreitol.

The lysate can be fractionated into a portion enriched for eukaryotic nucleic acids. The fractionation can be carried out, for example by centrifugation, filtration, targeted probes that specifically bind eukaryotic nucleic acid, antibodies, column-based filtration, bead-based filtration, or chromatographic methods. In some embodiments, fractionation by centrifugation can result in the formation of a bottom layer (a pellet), comprising cell debris, a hydrophilic middle layer comprising eukaryotic nucleic acids, and a hydrophobic top layer comprising lipids and membrane fractions. The middle layer can be collected. In some embodiments, the middle layer and the top layer can be collected together. The middle layer can be collected through a narrow bore orifice. The narrow bore orifice can be a pipette tip or a syringe fitted with a needle. The pipette tip can be, for example, a 1 uL, 5 uL, 10 uL, 20 uL, or 100 uL pipette tip. The needle can be, for example, an 18-gauge or a 15-gauge needle.

The collected layer comprising eukaryotic nucleic acids can be subjected to further extraction. The method of further extraction can vary. Exemplary methods include magnetic particle-based methods, column-based methods, filter-based methods, bead-based methods, or organic solvent-based methods. These exemplary methods can include commercially available reagents, for example Nuclisens® EasyMag® reagents (bioMerieux).

The extracted nucleic acids can be analyzed for eukaryotic biomarkers that are relevant to gastrointestinal disorders or gastrointestinal cells. The biomarkers can provide information on the health of an individual, i.e., the subject. These biomarkers from eukaryotic cells can include: a) a sequence of deoxyribonucleic acid (DNA), b) a sequence of ribonucleic acid (RNA), c) a predicted sequence of amino acids, which comprise the backbone of protein, d) expression levels or proportions of expression levels of RNA biomarkers, e) a predicted expression level or a predicted expression level proportion of an amino acid sequence, or f) any combination of the above. Isolation of biomarkers from eukaryotic cells can allow for comparison between an experimental sample and a control. Isolation of these biomarkers from eukaryotic cells can provide a method for detection of intestinal disease in the experimental sample. Comparison can include evaluation for: a) variation in a DNA sequence, b) variation in an RNA sequence, c) variation in the predicted amino acid sequence, d) variation in expression levels or the variation of the proportion of expression levels of RNA biomarkers, e) variation in the predicted expression level or variation in the prediction expression level proportion of an amino acid sequence, or f) a variation constituting any combination of the above. A variation can be determined when the measured biomarker of an experimental sample is different from the measured biomarker in a control.

The method can include obtaining an experimental sample and a control, for example, a stool sample. The stool sample contains sloughed off eukaryotic cells that can be evaluated for biomarkers. In some embodiments, the eukaryotic cells can be enterocytes, lymphocytes, enterochromiffin-like cells, entero-endocrine cells, neuro-endocrine cells, pancreatic cells, hepatic cells, gastric cells, or other cells. The method provides a way whereby the eukaryotic cells in the stool sample can be evaluated for eukaryotic biomarkers. The biomarkers can include a sequence of DNA, a sequence of RNA, a predicted sequence of amino acids, an expression level or proportion of expression level of RNA biomarkers, a predicted expression level or a predicted expression level proportion of an amino acid sequence, or any combination of the above. In specific embodiments, the biomarker is a stool-derived eukaryotic RNA biomarker. In some embodiments, the evaluation step comprises of any type of microarray sequencing, polymerase chain reaction (PCR), nucleic acid sequencing, amplicon sequencing, molecular barcoding, or probe-capture.

The methods and compositions are also useful for selecting a clinical plan for an individual suffering from a gastrointestinal disorder, for example, colorectal neoplasms or colorectal cancer. Through this method, the clinical plan can include administration of further diagnostic procedures, for example colonoscopy. In some embodiments, the clinical plan can include a method of treatment.

The levels of the stool-derived eukaryotic RNA biomarkers can be evaluated using a variety of methods. Expression levels can be determined either at the nucleic acid level, for example, the RNA level, or at the polypeptide level. RNA expression can encompass expression of seRNA, total RNA, mRNA, tRNA, rRNA, ncRNA, smRNA, miRNA, and snoRNA. Expression at the RNA level can be measured directly or indirectly by measuring levels of cDNA corresponding to the relevant RNA. Alternatively, or in addition, polypeptides encoded by the RNA, RNA regulators of the genes encoding the relevant transcription factors, and levels of the transcription factor polypeptides can also be assayed. Methods for determining gene expression at the mRNA level include, for example, microarray analysis, serial analysis of gene expression (SAGE), RT-PCR, blotting, hybridization based on digital barcode quantification assays, multiplex RT-PCR, droplet digital PCR (ddPCR), digital PCR (dPCR), NanoDrop spectrophotometers, RT-qPCR, qPCR, UV spectroscopy, amplicon sequencing, RNA sequencing, next-generation sequencing, lysate based hybridization assays utilizing branched DNA signal amplification such as the QuantiGene 2.0 Single Plex, and branched DNA analysis methods. Digital barcode quantification assays can include the BeadArray (Illumina), the xMAP systems (Luminex), the nCounter (NanoString), the HTG EdgeSe (High Throughput Genomics), BioMark (Fluidigm), or the Wafergen microarray. Assays can include DASL (Illumina), RNA-Seq (Illumina), TruSeq (Illumina), SureSelect (Agilent), Bioanalyzer (Agilent), TaqMan (ThermoFisher), GeneReader (Qiagen), or QIAseq (Qiagen).

We may use the terms "nucleic acid" and "polynucleotide" interchangeably to refer to both RNA and DNA, including cDNA, genomic DNA, synthetic DNA, and DNA (or RNA) containing nucleic acid analogs, any of which may encode a polypeptide of the invention and all of which are encompassed by the invention. Polynucleotides can have essentially any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA) and portions thereof, transfer RNA, micro RNA, ribosomal RNA, siRNA, microRNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs. In the context of the present invention, nucleic acids can encode a fragment of a biomarker, for example, stool-derived eukaryotic RNA biomarkers from any of the biomarkers listed in Table 1 and Table 2, or variant thereof or in Table 3 or a variant thereof or Table 4 or a variant thereof.

An "isolated" nucleic acid can be, for example, a DNA molecule or a fragment thereof, provided that at least one of the nucleic acid sequences normally found immediately flanking that DNA molecule in a genome is removed or absent. Thus, an isolated nucleic acid includes, without limitation, a DNA molecule that exists as a separate molecule, independent of other sequences (e.g., a chemically synthesized nucleic acid, or a cDNA or genomic DNA fragment produced by the polymerase chain reaction (PCR) or restriction endonuclease treatment). An isolated nucleic acid also refers to a DNA molecule that is incorporated into a vector, an autonomously replicating plasmid, a virus, or into the genomic DNA of a prokaryote or eukaryote. In addition, an isolated nucleic acid can include an engineered nucleic acid such as a DNA molecule that is part of a hybrid or fusion nucleic acid. A nucleic acid existing among many (e.g., dozens, or hundreds to millions) of other nucleic acids within, for example, cDNA libraries or genomic libraries, or gel slices containing a genomic DNA restriction digest, is not an isolated nucleic acid.

Isolated nucleic acid molecules can be produced in a variety of ways. For example, polymerase chain reaction (PCR) techniques can be used to obtain an isolated nucleic acid containing a nucleotide sequence described herein, including nucleotide sequences encoding a polypeptide described herein. PCR can be used to amplify specific sequences from DNA as well as RNA, including sequences from total genomic DNA or total cellular RNA. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid.

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >50-100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Two nucleic acids or the polypeptides they encode may be described as having a certain degree of identity to one another. For example, a stool-derived eukaryotic RNA biomarker selected from Table 1 or Table 2 or a combination of Table 1 and Table 2 or in Table 3 or Table 4 and a biologically active variant thereof may be described as exhibiting a certain degree of identity. Alignments may be assembled by locating short sequences in the Protein Information Research (PIR) site, followed by analysis with the "short nearly identical sequences" Basic Local Alignment Search Tool (BLAST) algorithm on the NCBI website.

As used herein, the term "percent sequence identity" refers to the degree of identity between any given query sequence and a subject sequence. For example, a stool-derived eukaryotic RNA biomarker sequence listed in Table 1 or Table 2 or a combination of Table 1 and Table 2 or in Table 3 or Table 4 can be the query sequence and a fragment of a stool-derived eukaryotic RNA biomarker sequence listed in Table 1 or Table 2 or a combination of Table 1 and Table 2 or in Table 3 or Table 4 can be the subject sequence. Similarly, a fragment of a stool-derived eukaryotic RNA biomarker sequence listed in Table 1 or Table 2 or a combination of Table 1 and Table 2 or in Table 3 or Table 4 can be the query sequence and a biologically active variant thereof can be the subject sequence.

To determine sequence identity, a query nucleic acid or amino acid sequence can be aligned to one or more subject nucleic acid or amino acid sequences, respectively, using a computer program, for example, ClustalW (version 1.83, default parameters), HISAT, HISAT2 or SAMTools, which allow alignments of nucleic acid or protein sequences to be carried out across their entire length (global alignment).

The nucleic acids and polypeptides described herein may be referred to as "exogenous". The term "exogenous" indicates that the nucleic acid or polypeptide is part of, or encoded by, a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the native sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found.

Nucleic acids of the invention can include nucleic acids having a nucleotide sequence of any one of the stool-derived eukaryotic RNA biomarkers listed in Table 1 or Table 2 or a combination of Table 1 and Table 2 or in Table 3 or Table 4, or a nucleic acid sequence that is at least about 70%, at least about 75%, at least about 80%, at least about 85%, at least about 90%, at least about 95%, at least about 99% identical to a nucleic acid sequence of any one of the stool-derived eukaryotic RNA biomarkers listed in Table 1 or Table 2 or a combination of Table 1 and Table 2 or in Table 3 or Table 4.

A nucleic acid, for example, an oligonucleotide (e.g., a probe or a primer) that is specific for a target nucleic acid will hybridize to the target nucleic acid under suitable conditions. We may refer to hybridization or hybridizing as the process by which an oligonucleotide single strand anneals with a complementary strand through base pairing under defined hybridization conditions. It is a specific, i.e., non-random, interaction between two complementary polynucleotides. Hybridization and the strength of hybridization (i.e., the strength of the association between the nucleic acids) is influenced by such factors as the degree of complementary between the nucleic acids, stringency of the conditions involved, and the melting temperature (Tm) of the formed hybrid. The hybridization products can be duplexes or triplexes formed with targets in solution or on solid supports.

In some embodiments, the nucleic acids can include short nucleic acid sequences useful for analysis and quantification of the stool-derived eukaryotic RNA biomarkers listed in Table 1 or Table 2 or a combination of Table 1 and Table 2 or in Table 3 or Table 4. Such isolated nucleic acids can be oligonucleotide primers. In general, an oligonucleotide primer is an oligonucleotide complementary to a target nucleotide sequence, for example, the nucleotide sequence of any of the stool-derived eukaryotic RNA biomarkers listed in Table 1 or Table 2 or a combination of Table 1 and Table 2 or in Table 3 or Table 4, that can serve as a starting point for DNA synthesis by the addition of nucleotides to the 3' end of the primer in the presence of a DNA or RNA polymerase. The 3' nucleotide of the primer should generally be identical to the target sequence at a corresponding nucleotide position for optimal extension and/or amplification. Primers can take many forms, including for example, peptide nucleic acid primers, locked nucleic acid primers, unlocked nucleic acid primers, and/or phosphorothioate modified primers. In some embodiments, a forward primer can be a primer that is complementary to the anti-sense strand of dsDNA and a reverse primer can be a primer that is complementary to the sense-strand of dsDNA. We may also refer to primer pairs. In some embodiments, a 5' target primer pair can be a primer pair that includes at least one forward primer and at least one reverse primer that amplifies the 5' region of a target nucleotide sequence. In some embodiments, a 3' target primer pair can be a primer pair at least one forward primer and at least one reverse primer that amplifies the 3' region of a target nucleotide sequence. In some embodiments, the primer can include a detectable label, as discussed below. In some embodiments, the detectable label can be a quantifiable label.

Oligonucleotide primers provided herein are useful for amplification of any of the stool-derived eukaryotic RNA biomarkers listed in Table 1 and Table 2 or in Table 3 or Table 4. In some embodiments, oligonucleotide primers can be complementary to 2, 3, 4, 5, 6, 7, 8, 9, 10, 11, 12, 13, 14, 15, 16, 17, 18, 19, 20, 21, 22, 23, 24, 25, 26, 27, 28, 29, 30 or more of the stool-derived eukaryotic RNA biomarkers disclosed herein, for example, the stool-derived eukaryotic RNA biomarkers listed in Table 1 and Table 2 or in Table 3 or Table 4. The primer length can vary depending upon the nucleotide base sequence and composition of the particular nucleic acid sequence of the probe and the specific method for which the probe is used. In general, useful primer lengths can be about 8, 9, 10, 11, 12, 13, 14, 15, 16, 17, 18, 19, 20, 21, 22, 23, 24, 25, 26, 27, 28, 29, 30 nucleotide bases. Useful primer lengths can range from 8 nucleotide bases to about 60 nucleotide bases; from about 12 nucleotide bases to about 50 nucleotide bases; from about 12 nucleotide bases to about 45 nucleotide bases; from about 12 nucleotide bases to about 40 nucleotide bases; from about 12 nucleotide bases to about 35 nucleotide bases; from about 15 nucleotide bases to about 40 nucleotide bases; from about 15 nucleotide bases to about 35 nucleotide bases; from about 18 nucleotide bases to about 50 nucleotide bases; from about 18 nucleotide bases to about 40 nucleotide bases; from about 18 nucleotide bases to about 35 nucleotide bases; from about 18 nucleotide bases to about 30 nucleotide bases; from about 20 nucleotide bases to about 30 nucleotide bases; from about 20 nucleotide bases to about 25 nucleotide bases.

Also provided are probes, that is, isolated nucleic acid fragments that selectively bind to and are complementary to any of the stool-derived eukaryotic RNA biomarkers listed in Table 1 and Table 2 or in Table 3 or Table 4. Probes can be oligonucleotides or polynucleotides, DNA or RNA, single- or double-stranded, and natural or modified, either in the nucleotide bases or in the backbone. Probes can be produced by a variety of methods including chemical or enzymatic synthesis.

The probe length can vary depending upon the nucleotide base sequence and composition of the particular nucleic acid sequence of the probe and the specific method for which the probe is used. In general, useful probe lengths can be about 8, 9, 10, 11, 12, 13, 14, 15, 16, 17, 18, 19, 20, 21, 22, 23, 24, 25, 26, 27, 28, 29, 30, 35, 40, 50, 55, 60, 65, 70, 75, 80, 85, 90, 100, 110, 120, 140, 150, 175, or 200 nucleotide bases. In general, useful probe lengths will range from about 8 to about 200 nucleotide bases; from about 12 to about 175 nucleotide bases; from about 15 to about 150 nucleotide bases; from about 15 to about 100 nucleotide bases from about 15 to about 75 nucleotide bases; from about 15 to about 60 nucleotide bases; from about 20 to about 100 nucleotide bases; from about 20 to about 75 nucleotide bases; from about 20 to about 60 nucleotide bases; from about 20 to about 50 nucleotide bases in length. In some embodiments the probe set can comprise probes directed to 2, 3, 4, 5, 6, 7, 8, 9, 10, 11, 12, 13, 14, 15, 16, 17, 18, 19, 20, 21, 22, 23, 24, 25, 26, 27, 28, 29, 30 or more of the stool-derived eukaryotic RNA biomarkers listed in Table 1 or Table 2 or a combination of Table 1 and Table 2 or in Table 3 or Table 4.

The primers and probes disclosed herein can be detectably labeled. A label can be a molecular moiety or compound that can be detected or lead to a detectable response, which may be joined directly or indirectly to a nucleic acid. Direct labeling may use bonds or interactions to link label and probe, which includes covalent bonds, non-covalent interactions (hydrogen bonds, hydrophobic and ionic interactions), or chelates or coordination complexes. Indirect labeling may use a bridging moiety or linker (e.g. antibody, oligomer, or another compound), which is directly or indirectly labeled, which may amplify a signal. Labels include any detectable moiety, e.g., radionuclide, ligand such as biotin or avidin, enzyme, enzyme substrate, reactive group, chromophore (detectable dye, particle, or bead), fluorophore, or luminescent compound (bioluminescent, phosphorescent, or chemiluminescent label). Labels can be detectable in a homogeneous assay in which bound labeled probe in a mixture exhibits a detectable change compared to that of unbound labeled probe, e.g., stability or differential degradation, without requiring physical separation of bound from unbound forms.

Suitable detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.). As discussed above, coupling of the one or more ligand motifs and/or ligands to the detectable label may be direct or indirect. Detection may be in situ, in vivo, in vitro on a tissue section or in solution, etc.

In some embodiments, the methods include the use of alkaline phosphatase conjugated polynucleotide probes. When an alkaline phosphatase (AP)-conjugated polynucleotide probe is used, following sequential addition of an appropriate substrate such as fast blue or fast red substrate, AP breaks down the substrate to form a precipitate that allows in-situ detection of the specific target RNA molecule. Alkaline phosphatase may be used with a number of substrates, e.g., fast blue, fast red, or 5-Bromo-4-chloro-3-indolyl-phosphate (BCIP).

In some embodiments, the fluorophore-conjugates probes can be fluorescent dye conjugated label probes, or utilize other enzymatic approaches besides alkaline phosphatase for a chromogenic detection route, such as the use of horseradish peroxidase conjugated probes with substrates like 3,3'-Diaminobenzidine (DAB).

The fluorescent dyes used in the conjugated label probes may typically be divided into families, such as fluorescein and its derivatives; rhodamine and its derivatives; cyanine and its derivatives; coumarin and its derivatives; Cascade Blue™ and its derivatives; Lucifer Yellow and its derivatives; BODIPY and its derivatives; and the like. Exemplary fluorophores include indocarbocyanine (C3), indodicarbocyanine (C5), Cy3, Cy3.5, Cy5, Cy5.5, Cy7, Texas Red, Pacific Blue, Oregon Green 488, Alexa Fluor®-355, Alexa Fluor 488, Alexa Fluor 532, Alexa Fluor 546, Alexa Fluor-555, Alexa Fluor 568, Alexa Fluor 594, Alexa Fluor 647, Alexa Fluor 660, Alexa Fluor 680, JOE, Lissamine, Rhodamine Green, BODIPY, fluorescein isothiocyanate (FITC), carboxy-fluorescein (FAM), phycoerythrin, rhodamine, dichlororhodamine (dRhodamine™), carboxy tetramethylrhodamine (TAMRA™), carboxy-X-rhodamine (ROX™) LIZ™, VIC™, NED™, PET™, SYBR, PicoGreen, RiboGreen, and the like. Near-infrared dyes are expressly within the intended meaning of the terms fluorophore and fluorescent reporter group.

In some embodiments, levels of the eukaryotic biomarkers can be analyzed on a gene array. Microarray analysis can be performed on a customized gene array. Alternatively, or in addition, microarray analysis can be carried out using commercially-available systems according to the manufacturer's instructions and protocols. Exemplary commercial systems include Affymetrix GENECHIP® technology (ThermoFisher, Walthum, Mass.), Agilent microarray technology, the NCOUNTER® Analysis System (NanoString® Technologies, Seattle, Wash.) and the BeadArray Microarray Technology (Illumina, San Diego, Calif.). Nucleic acids extracted from a stool sample can be hybridized to the probes on the gene array. Probe-target hybridization can be detected by chemiluminescence to determine the relative abundance of particular sequences. Relative abundances of particular sequences can be normalized across a gene array or within a gene array.

In some embodiments, the probes and probe sets can be configured as a gene array. A gene array, also known as a microarray or a gene chip, is an ordered array of nucleic acids that allows parallel analysis of complex biological samples. Typically, a gene array includes probes that are attached to a solid substrate, for example a microchip, a glass slide, or a bead. The attachment generally involves a chemical coupling resulting in a covalent bond between the substrate and the probe. The number of probes in an array can vary, but each probe is fixed to a specific addressable location on the array or microchip. In some embodiments, the probes can be about 18 nucleotide bases, about 20 nucleotide bases, about 25 nucleotide bases, about 30 nucleotide bases, about 35 nucleotide bases, or about 40 nucleotide bases in length. In some embodiments, the probe set comprises probes directed to at least 2, 3, 4, 5, 6, 7, 8, 9, 10, 11, 12, 13, 14, 15, 16, 17, 18, 19, 20, 21, 22, 23, 24, 25, 26, 27, 28, 29, 30 or more of the stool-derived eukaryotic RNA biomarkers listed in Table 1 or Table 2 or a combination of Table 1 and Table 2 or in Table 3 or Table 4. The probe sets can be incorporated into high-density arrays comprising 5,000, 10,000, 20,000, 50,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000 or more different probes.

Methods of gene array synthesis can vary. Exemplary methods include synthesis of the probes followed by deposition onto the array surface by "spotting," in situ synthesis, using for example, photolithography, or electrochemistry on microelectrode arrays.

In some embodiments, the probes and probe sets can be configured as a reagent, that is, a pool of nucleic acids that allows parallel analysis of complex biological samples. A reagent, can be, for example, a set of amplification probes, a library preparation, an amplicon panel, or a capture panel. Typically, a reagent includes targeted probes that are suspended in a solution. In some embodiments the probes are designed to target specific regions. The probes can be configured in a way that allows for capture of specific nucleic acids. The probes can also be configured to allow for amplification of a specific nucleic acid. The number of probes in a reagent can vary, but each probe is designed to a specific sequence. In some embodiments, the probes can be about 10 nucleotide bases, about 15 nucleotide bases, about 20 nucleotide bases, about 25 nucleotide bases, about 30 nucleotide bases, about 35 nucleotide bases, or about 40 nucleotide bases in length. In some embodiments, the probe set comprises probes directed to at least 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers listed in Table 1 or Table 2 or a combination of Table 1 and Table 2 or in Table 3 or Table 4. The probe sets can be incorporated into high-density reagents comprising 5,000, 10,000, 20,000, 50,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000 or more different probes.

Methods of reagent synthesis can vary. Exemplary methods include synthesis of nucleic acid probes followed by suspension in a stabilization solution. Probe reagents can contain a unique region that serves as a molecular identifier. The reagents can be used for such methods as PCR, rtPCR ddPCR, dPCR, next-generation sequencing, amplicon sequencing, RNA-se, and other methods.

Levels of the eukaryotic biomarkers can also be analyzed by DNA sequencing. DNA sequencing can be performed by sequencing methods such as targeted sequencing, whole genome sequencing, amplicon sequencing, or exome sequencing. Sequencing methods can include: Sanger sequencing or high-throughput sequencing. High throughput sequencing can involve sequencing-by-synthesis, pyrosequencing, sequencing-by-ligation, real-time sequencing, nanopore sequencing, or Sanger sequencing. In some embodiments, isolated RNA can be used to generate a corresponding cDNA and the cDNA can be sequenced.

The sequencing methods described herein can be carried out in multiplex formats such that multiple different target nucleic acids are manipulated simultaneously. In some embodiments, different target nucleic acids can be treated in a common reaction vessel or on a surface of a particular substrate, enabling convenient delivery of sequencing reagents, removal of unreacted reagents, and detection of incorporation events in a multiplex manner. In some embodiments where surface-bound target nucleic acids are involved, the target nucleic acids may be in an array format. In an array format, the target nucleic acids may be typically coupled to a surface in a spatially distinguishable manner. For example, the target nucleic acids may be bound by direct covalent attachment, attachment to a bead or other particle, or associated with a polymerase or other molecule that is attached to the surface. The array may include a single copy of a target nucleic acid at each site (also referred to as a feature) or multiple copies having the same sequence can be present at each site or feature. Multiple copies are produced by amplification methods such as bridge amplification, amplicon amplification, PCR, or emulsion PCR.

In some embodiments, a normalization step can be used to control for nucleic acid recovery and variability between samples. In some embodiments, a defined amount of exogenous control nucleic acids can be added ("spiked in") to the extracted eukaryotic nucleic acids. The exogenous control nucleic acid can be a nucleic acid having a sequence corresponding to one or more eukaryotic or non-eukaryotic sequences, for example, a PhiX. Alternatively, or in addition, the exogenous control nucleic acid can have a sequence corresponding to the sequence found in another species, for example a bacterial sequence such as a *Bacillus subtilis* sequence. In some embodiments, the methods can include determining the levels of one or more housekeeping genes. In some embodiments, the methods can include normalizing the expression levels of biomarkers to the levels of the housekeeping genes.

The methods include the step of determining whether the measured expression levels of 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers in an experimental sample are different from the measured expression levels of the same 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers in a control. In another embodiment, the methods include the step of determining whether the proportion of expression levels of 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers in an experimental sample are different from the proportion of measured expression levels of the same 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers in a control. A difference in the expression levels or the proportion of expression levels can be an increase or a decrease.

The compositions disclosed herein are generally and variously useful for the detection, diagnosis and treatment of colorectal neoplasms. Methods of detection can include measuring the expression level in a stool sample of 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers selected from the biomarkers listed in Table 1 or Table 2 or a combination of Table 1 and Table 2 or in Table 3 or Table 4, and comparing the measured expression level of the 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers selected from the biomarkers listed in Table 1 or Table 2 or a combination of Table 1 and Table 2 or in Table 3 or Table 4, in the sample with the measured expression level of 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers selected from the biomarkers listed in Table 1 or Table 2 or a combination of Table 1 and Table 2 or in Table 3 or Table 4 in a control. A difference in the measured expression level of 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers selected from the biomarkers listed in Table 1 or Table 2 or a combination of Table 1 and Table 2 in a patient's sample relative to the measured expression level of the 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers selected from the biomarkers listed in Table 1 or Table 2 or a combination of Table 1 and Table 2 in a control is an indication that the patient has a colorectal neoplasm, or more specifically, a high-risk adenoma. In some embodiments, a difference in the measured expression level of 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers selected from the biomarkers listed in Table 1 or Table 2 or a combination of Table 1 and Table 2 in a patient's sample relative to the measured expression level of 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers selected from the biomarkers listed in Table 1 or Table 2 or a combination of Table 1 and Table 2 in a control is an indication that the patient is at risk for a colorectal neoplasm, or more specifically, a high-risk adenoma. These methods can further include the step of identifying a subject (e.g., a patient and, more specifically, a human patient) who has a colorectal neoplasm, for example, colorectal cancer or a precancerous lesion, or who is at risk for developing a colorectal neoplasm.

A difference in the variant allele frequency of 1, 2, 3, 4, 5, 6, 7, 8, 9, 10, 11, 12, 13, 14, 15, 16, 17, or 18 stool-derived eukaryotic RNA variant biomarkers selected from the biomarkers listed in Table 3 in a subject's sample relative to the variant allele frequency of the 1, 2, 3, 4, 5, 6, 7, 8, 9, 10, 11, 12, 13, 14, 15, 16, 17, or 18 stool-derived eukaryotic RNA variant biomarkers selected from the biomarkers listed in Table 3 in a control is an indication that the patient has a colorectal neoplasm. In some embodiments, a difference in the measured variant allele frequency of 1, 2, 3, 4, 5, 6, 7, 8, 9, 10, 11, 12, 13, 14, 15, 16, 17, or 18 stool-derived eukaryotic RNA biomarkers selected from the biomarkers listed in Table 3 in a patient's sample relative to the measured variant allele frequency of 2, 3, 4, 5, 6, 7, 8, 9, 10, 11, 12, 13, 14, 15, 16, 17, or 18 stool-derived eukaryotic RNA biomarkers selected from the biomarkers listed in Table 3 in a control is an indication that the patient is at risk for a colorectal neoplasia. These methods can further include the step of identifying a subject (e.g., a patient and, more specifically, a human patient) who has colorectal neoplasia, for example, colorectal cancer or a precancerous lesion, or who is at risk for developing a colorectal neoplasm.

A difference in the measured expression level of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers selected from the colorectal neoplasm molecular subtype biomarker genes listed in FIGS. 4A-4B in a patient's sample relative to the measured expression level of the 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers selected from the colorectal neoplasm molecular subtype biomarker genes listed in FIGS. 4A-4B in a control is an indication that the patient has a molecular subtype of colorectal cancer, for example, CMS1. In some embodiments, a difference in the measured expression level of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers selected from the colorectal neoplasm molecular subtype biomarker genes listed in FIGS. 4A-4B in a patient's sample relative to the measured expression level of 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers selected from the colorectal neoplasm molecular subtype biomarker genes listed in FIGS. 4A-4B in a control is an indication that the patient is at risk for a molecular subtype of the colorectal cancer, for example, CMS1. These methods can further include the step of identifying a subject (e.g., a patient and, more specifically, a human patient) who has colorectal neoplasia, for example, colorectal cancer or a precancerous lesion, or who is at risk for developing a colorectal neoplasm.

A colorectal neoplasm can include any form of colorectal cancer. A colorectal neoplasm can also include a polyp, for example a precancerous lesion. Colorectal cancer typically begins as a growth, termed a polyp, in the luminal lining of the colon or rectum. Colorectal polyps are generally divided into two categories: adenomatous polyps and benign polyps. Adenomatous polyps can also be called adenomas. Benign polyps can also be called hyperplastic polyps, hamartomatous polyps, or inflammatory polyps. A patient with an adenomatous polyp or multiple adenomatous polyps can be classified as having high-risk adenomas, medium-risk adenomas, or low-risk adenomas. High-risk adenomas include adenomas with carcinoma in situ or high-grade dysplasia of any size, adenomas with greater than or equal to 25% villous growth pattern of any size, any adenomas greater than or equal to 1.0 cm in size, or any serrated lesion greater than or equal to 1.0 cm in size. Medium-risk adenomas include 1 or 2 non-high-risk adenomas ranging 5.0 mm to 1.0 cm in size or greater than or equal to 3 non-high-risk adenomas less than 1.0 cm in size. Low-risk adenomas include 1 or 2 non-high-risk adenomas less than or equal to 5.0 mm in size. Adenomatous polyps can give rise to colorectal cancer. The most common form of colorectal cancer, adenocarcinoma, originates in the intestinal gland cells that line the inside of the colon and/or rectum. Adenocarcinomas can include tubular adenocarcinomas, which are glandular cancers on a pedunculated stalk. Adenocarcinomas can also include villous adenocarcinomas, which are glandular cancers that lie flat on the surface of the colon. Other colorectal cancers are distinguished by their tissue of origin. These include gastrointestinal stromal tumors (GIST), which arise from the interstitial cells of Cajal; primary colorectal lymphomas, which arise from hematologic cells; leiomyosarcomas, which are sarcomas arising from connective tissue or smooth muscle; melanomas, which arise from melanocytes: squamous cell carcinomas which arise from stratified squamous epithelial tissue and are confined to the rectum; and mucinous carcinomas, which are epithelial cancers generally associated with poor prognosis.

Symptoms of colorectal neoplasia or colorectal cancer can include, but are not limited to, a change in bowel habits, including diarrhea or constipation or a change in the consistency of the stool lasting longer than four weeks, rectal bleeding or blood in the stool, persistent abdominal discomfort such as cramps, gas or pain, a feeling that the bowel does not empty completely, weakness or fatigue, and unexplained weight loss. Patients suspected of having colorectal neoplasia or colorectal cancer may receive peripheral blood tests, including a complete blood count (CBC), a fecal occult blood test (FOBT), a liver function analysis, a fecal immunochemical test (FIT), and/or other analysis of certain tumor markers, for example carcinoembryonic antigen (CEA) and CA19-9. Colorectal neoplasia or colorectal cancer is often diagnosed based on colonoscopy. During colonoscopy, any polyps that are identified are removed, biopsied, and analyzed to determine whether the polyp contains colorectal cancer cells or cells that have undergone a precancerous change. Each one of the specific cancers listed above can look different when viewed through an endoscope. Villous adenomas melanomas, and squamous cell carcinomas are typically flat or sessile, whereas tubular adenomas, lymphomas, leiomyosarcomas, and GIST tumors are typically pedunculated. However, flat and sessile adenomas can be missed by gastroenterologists during colonoscopies. Biopsy samples can be subjected to further analysis based on genetic changes of particular genes or microsatellite instability.

Other diagnostic methods can include, sigmoidoscopy; imaging tests, for example, computed tomography (CT or CAT) scans; ultrasound, for example abdominal, endorectal or intraoperative ultrasound; or magnetic resonance imaging (MRI) scans, for example endorectal MRI. Other tests such as angiography and chest x-rays can be carried out to determine whether a colorectal cancer has metastasized.

A variety of methods for staging colorectal cancer have been developed. The most commonly used system, the TNM system is based on three factors: 1) the distance that the primary tumor (T) has grown into the wall of the intestine and nearby areas; 2) whether the tumor has spread to nearby regional lymph nodes (N); 3) whether the cancer has metastasized to other organs (M). Other methods of staging include Dukes staging and the Astler-Coller classification.

The TNM system provides a four-stage classification of colorectal cancer. In Stage 1 (T1) colorectal cancer, the tumor has grown into the layers of the colon wall, but has not spread outside the colon wall or into lymph nodes. If the cancer is part of a tubular adenoma polyp, then simple excision is performed and the patient can continue to receive routine testing for future cancer development. If the cancer is high grade or part of a flat/sessile polyp, more surgery might be required and larger margins will be taken; this might include partial colectomy where a section of the colon is resected. In Stage 2 (T2) colorectal cancer, the tumor has grown into the wall of the colon and potentially into nearby tissue but has not spread to nearby lymph nodes. Surgical removal of the tumor and a partial colectomy is generally performed. Adjunct therapy, for example, chemotherapy with agents such as 5-fluorouracil, leucovorin, or capecitabine, may be administered. Such tumors are unlikely to recur, but increased screening of the patient is generally needed. In Stage 3 (T3) colorectal cancer, the tumor has spread to nearby lymph nodes, but not to other parts of the body. Surgery to remove the section of the colon and all affected lymph nodes will be required. Chemotherapy, with agents such as 5-fluorouracil, leucovorin, oxaliplatin, or capecitabine combined with oxaliplatin is typically recommended. Radiation therapy may also be used depending on the age of the patient and aggressive nature of the tumor. In Stage 4 (T4) colorectal cancer, the tumor has spread from the colon to distant organs through the blood. Colorectal cancer most frequently metastasizes to the liver, lungs and/or peritoneum. Surgery is unlikely to cure these cancers and chemotherapy and or radiation are generally needed to improve survival rates.

The methods disclosed herein are generally useful for diagnosis and treatment of colorectal neoplasia. The expression level of 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers, for example a stool-derived eukaryotic RNA biomarker selected from Table 1 or Table 2 or a combination of Table 1 and Table 2 or in Table 3 or Table 4, is measured in a biological sample, for example a stool sample from a subject. The subject can be a patient having one or more of the symptoms described above that would indicate the patient is at risk for colorectal cancer. The subject can also be a patient having no symptoms, but who may be at risk for colorectal neoplasia based on age (for example, above age 50), family history, obesity, diet, alcohol consumption, tobacco use, previous diagnosis of colorectal polyps, race and ethnic background, inflammatory bowel disease, and genetic syndromes, such as familial adenomatous polyposis, Gardner syndrome, Lynch syndrome, Turcot syndrome, Peutz-Jeghers syndrome, and MUTYH-associated polyposis, associated with higher risk of colorectal cancer. The methods disclosed herein are also useful for monitoring a patient who has previously been diagnosed and treated for colorectal neoplasia or colorectal cancer in order to monitor remission and detect lesion recurrence.

In some embodiments, the disease-state of a subject, that is, a human or non-human animal patient, is determined by pathological evaluation. For example, in one type of disease, such as colorectal cancer, the extent of disease is classified as stage 1 (T1), stage 2 (T2), stage 3 (T3), and stage 4 (T4). The colorectal cancer can be a tubular adenocarcinoma, a villous adenocarcinoma, a gastrointestinal stromal tumor, a primary colorectal lymphoma, a leiomyosarcoma, melanoma, a squamous cell carcinoma, or a mucinous carcinoma. In another type of disease, such as inflammatory bowel disease, the disease-state is determined by location of the disease along the intestinal tract and histological features such as granulomas, leukocyte infiltrates, and/or crypt abscesses. Other methods for determining disease-state such as physician determination, physical symptoms, fecal occult blood test, a fecal immunochemical test, sigmoidoscopy, FIT-DNA, CT Colonography, or a colonoscopy can also be used in conjunction with the methods disclosed herein.

Also provided are methods of determining whether a subject is at risk for intestinal disease. Intestinal disease can include intestinal cancer, colorectal cancer, adenomatous polyps indicative of precancerous change, irritable bowel syndrome, necrotizing enterocolitis, ulcerative colitis, Crohn's disease celiac disease, or other intestinal disease. The method of determining whether a subject is at risk for intestinal disease can be determined by using the invention to detect a) a sequence of deoxyribonucleic acid (DNA), b) a sequence of ribonucleic acid (RNA), c) a predicted amino acid sequence, which comprises the backbone of protein, d) expression levels of ribonucleic acid biomarkers, e) prediction in the variation of a sequence in amino acid, or f) any combination of the above, wherein a difference between the control and the experimental sample can indicate that the subject is at risk for intestinal disease.

The methods and compositions are also useful for selecting a clinical plan for a subject with intestinal disease. Through this method, the clinical plan can include administration of further diagnostic procedures. In some embodiments, the clinical plan can include a method of treatment.

Algorithms for determining diagnosis, status, or response to treatment, for example, can be determined for particular clinical conditions. The algorithms used in the methods provided herein can be mathematic functions incorporating multiple parameters that can be quantified using, without limitation, medical devices, clinical evaluation scores, or biological/chemical/physical tests of biological samples. Each mathematic function can be a weight-adjusted expression of the levels (e.g., measured levels) of parameters determined to be relevant to a selected clinical condition. Because of the techniques involved in weighting and assessing multiple marker panels, computers with reasonable computational power can be used to analyze the data.

Thus, the method of diagnosis can include obtaining a stool sample from a patient at risk for or suspected of having a colorectal neoplasm; determining the expression of 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers selected from the stool-derived eukaryotic RNA biomarkers listed in Table 1 or Table 2 or a combination of Table 1 and Table 2 or in Table 3 or Table 4, and providing a test value by the machine learning algorithms that incorporate a plurality of stool-derived eukaryotic RNA biomarkers with a predefined coefficient. Exemplary machine learning algorithms include Support Vector Machine, Gradient Boosting, Adaptive Boosting, Random Forest, Naive Bayes, Decision Tree, and k-Nearest Neighbors, or others. A significant change in expression of a plurality of colorectal neoplasm biomarkers relative to the control, for example, a population of healthy individuals, indicates an increased likelihood that the patient has colorectal neoplasia. In some embodiments, the expression levels measured in a sample are used to derive or calculate a probability or a confidence score. This value may be derived from expression levels. Alternatively, or in addition, the value can be derived from a combination of the expression levels with other factors, for example, the patient's medical history, ethnicity, gender, age, smoking status, previous genomic results, previous histopathology results, and genetic background. Alternatively, or in addition, the value can be derived from a combination of the expression levels with a fecal immunochemical test (FIT). In some embodiments, the method can further comprise the step of communicating the test value to the patient. This method could include, for example, visual representation of the markers, numerical output of the markers, or other methods of communication.

In some embodiments, a prediction for one or more patients can be generated using a model-based approach. For example, in some embodiments, a random forest model may be configured to predict disease absence, disease presence and/or disease severity in one or more groups, such as colorectal cancer, HRAs, MRAs, LRAs, benign polyps, or no findings. In some embodiments, a validation dataset and/or a test dataset may be applied to test or refine the model. Once generated, the model is used to predict disease absence, disease presence and/or disease severity of one or more specific patients based on the provided inputs, such as, for example, a plurality of amplicons. Although specific embodiments are discussed herein, it will be appreciated that any suitable model could include any number of decision trees, nodes, input layers, output layers, hidden layers or other varied parameters. In some embodiments, a random forest model using a greater and/or lesser number of decision trees, a greater and/or lesser number of eligible features, etc. may be generated.

In some embodiments, the one or more models may be generated, tested, and/or executed using a system configured for disease detection. In some embodiments, the system includes a computer system having one or more processors. Each processor is connected to a communication infrastructure (e.g., a communications bus, cross-over bar, or network). The processor can be implemented as a central processing unit, an embedded processor or microcontroller, an application-specific integrated circuit (ASIC), and/or any other circuit configured to execute computer executable instructions to perform one or more steps. Processors are similar to the processor discussed above and similar description is not repeated herein. Computer system may include a display interface that forwards graphics, text, and other data from the communication infrastructure (or from a frame buffer) for display on the display unit to a user.

Computer system may also include a main memory, such as a random access memory (RAM), and a secondary memory. The main memory and/or the secondary memory comprise a dynamic random access memory (DRAM). The secondary memory may include, for example, a hard disk drive (HDD) and/or removable storage drive, which may represent a solid state memory, an optical disk drive, a flash drive, a magnetic tape drive, or the like. The removable storage drive reads from and/or writes to a removable storage unit. Removable storage unit may be an optical disk, magnetic disk, floppy disk, magnetic tape, or the like. The removable storage unit may include a computer readable storage medium having tangibly stored therein (or embodied thereon) data and/or computer executable software instructions, e.g., for causing the processor(s) to perform various operations and/or one or more steps.

In alternative embodiments, secondary memory may include other devices for allowing computer programs or other instructions to be loaded into computer system. Secondary memory may include a removable storage unit and a corresponding removable storage interface, which may be similar to removable storage drive, with its own removable storage unit. Examples of such removable storage units include, but are not limited to, universal serial bus (USB) or flash drives, which allow software and data to be transferred from the removable storage unit to computer system.

Computer system may also include a communications interface (e.g., networking interface). Communications interface allows instructions and data to be transferred between computer system and one or more additional systems. Communications interface also provides communications with other external devices. Examples of communications interface may include a modem, Ethernet interface, wireless network interface (e.g., radio frequency, IEEE 802.11 interface, Bluetooth interface, or the like), a Personal Computer Memory Card International Association (PCMCIA) slot and card, or the like. Instructions and data transferred via communications interface may be in the form of signals, which may be electronic, electromagnetic, optical, or the like that are capable of being received by communications interface. These signals may be provided to communications interface via a communications path (e.g., channel), which may be implemented using wire, cable, fiber optics, a telephone line, a cellular link, a radio frequency (RF) link and other communication channels.

The methods and system described herein may be at least partially embodied in the form of computer-implemented processes and apparatus for practicing those processes. The disclosed methods may also be at least partially embodied in the form of tangible, non-transitory machine-readable storage media encoded with computer executable program code. The media may include, for example, RAMs, ROMs, CD-ROMs, DVD-ROMs, BD-ROMs, hard disk drives, flash memories, or any other non-transitory machine-readable storage medium, wherein, when the computer program code is loaded into and executed by a computer, the computer becomes an apparatus for practicing the method. The methods may also be at least partially embodied in the form of a computer into which computer program code is loaded and/or executed, such that, the computer becomes a special purpose computer for practicing the methods. When implemented on a general-purpose processor, the computer program code segments configure the processor to create specific connections, circuits, and algorithms for implementing the methods disclosed herein.

Standard computing devices and systems can be used and implemented, e.g., suitably programmed, to perform the methods described herein, e.g., to perform the calculations needed to determine the values described herein. Computing devices include various forms of digital computers, such as laptops, desktops, mobile devices, workstations, personal digital assistants, servers, blade servers, mainframes, and other appropriate computers. In some embodiments, the computing device is a mobile device, such as personal digital assistant, cellular telephone, smartphone, tablet, or other similar computing device.

In some embodiments, a computer can be used to communicate information, for example, to a healthcare professional. Information can be communicated to a professional by making that information electronically available (e.g., in a secure manner). For example, information can be placed on a computer database such that a health-care professional can access the information. In addition, information can be communicated to a hospital, clinic, or research facility serving as an agent for the professional. Information transferred over open networks (e.g., the internet or e-mail) can be encrypted. Patient's gene expression data and analysis can be stored in the cloud with encryption. The method 256-bit AES with tamper protection can be used for disk encryption; SSL protocol preferably can ensure protection in data transit, and key management technique SHA2-HMAC can allow authenticated access to the data. Other secure data storage means can also be used.

The results of such analysis above, e.g., a probability or confidence score derived from a combination of expression levels with other factors, for example, the patient's medical history, ethnicity, gender, age, smoking status, previous genomic results, previous histopathology results, genetic background, or a fecal immunochemical test (FIT), can be the basis of follow-up and treatment by the attending clinician. If the expression level of 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers, for example a stool-derived eukaryotic RNA biomarker selected from Table 1 or Table 2 or a combination of Table 1 and Table 2 or in Table 3 or Table 4, is not significantly different from the expression level of the same stool-derived eukaryotic RNA biomarker in a control, the clinician may determine that the patient is presently not at risk for colorectal neoplasms. Such patients can be encouraged to return in the future for rescreening. The extent to which the expression level of 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers, for example a stool-derived eukaryotic RNA biomarker selected from Table 1 or Table 2 or a combination of Table 1 and Table 2 or in Table 3 or Table 4, is not significantly different from the expression level of the same stool-derived eukaryotic RNA biomarker in a control can be used to determine the duration of time before required follow-up. In some embodiments, the clinician can recommend that the patient return for follow-up in 1 month, 2 months, 3 months, 6 months, 1 year, 2 years, 3 years, 5 years, or 10 years. The methods disclosed herein can be used to monitor any changes in the levels of the colorectal neoplasm markers over time. A subject can be monitored for any length of time following the initial screening and/or diagnosis. For example, a subject can be monitored for at least 2, 4, 6, 8, 10, 12, 14, 16, 18, 20, 25, 30, 35, 40, 45, 50, 55, or 60 months or more or for at least 1, 2, 3, 4, 5, 6, 7, 8, 9, 10, 11, 12, 13, 14, 15, 16, 17, 18, 19, 20 or more years.

The methods and compositions disclosed herein are useful for selecting a clinical plan for a subject at risk for or suffering from colorectal neoplasia or colorectal cancer. The clinical plan can include administration of further diagnostic procedures, for example, a fecal occult blood test, a fecal immunochemical test, or a colonoscopy to remove cancer, polyps, or precancerous lesions. In some embodiments, the clinical plan can include a method of treatment. In some embodiments, the methods include selecting a treatment for a subject having a colorectal neoplasm or colorectal cancer. If the expression level of 2, 3, 4, 5, 6, 7, 8, 9, 10, 11, 12, 13, 14, 15, 16, 17, 18, 19, 20, 21, 22, 23, 24, 25, 26, 27, 28, 29, 30 or more of the stool-derived eukaryotic RNA biomarkers selected from Table 1 or Table 2 or a combination of Table 1 and Table 2 or Table 3 or Table 4, is significantly different from the expression level of the same 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers in a control, the patient may have colorectal neoplasms or colorectal cancer. In these instances, further screening may be recommended, for example, increased frequency of screening using the methods disclosed herein, as well as a fetal occult blood test, a fecal immunochemical test, and/or a colonoscopy. If the expression level of 2, 3, 4, 5, 6, 7, 8, 9, 10, 11, 12, 13, 14, 15, 16, 17, 18, 19, 20, 21, 22, 23, 24, 25, 26, 27, 28, 29, 30 or more of the stool-derived eukaryotic RNA biomarkers selected from Table 1 or Table 2 or a combination of Table 1 and Table 2 or Table 3 or Table 4 is significantly different from the expression level of the same 2, 3, 4, 5, 6, 7, 8, 9, 10, 11, 12, 13, 14, 15, 16, 17, 18, 19, 20, 21, 22, 23, 24, 25, 26, 27, 28, 29, 30 or more of the stool-derived eukaryotic RNA biomarkers selected from Table 1 or Table 2 or a combination of Table 1 and Table 2 or Table 3 or Table 4 in a control, the patient may have a particular type of colorectal neoplasm, for example, a high-risk adenoma. In some embodiments, treatment may be recommended, including, for example, a colonoscopy with removal of polyps, chemotherapy, immunotherapy, or surgery, such as bowel resection. Thus, the methods can be used to determine the level of expression of 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers, for example, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more of the stool-derived eukaryotic RNA biomarkers selected from Table 1 or Table 2 or a combination of Table 1 and Table 2 or Table 3 or Table 4 or a variant thereof and then to determine a course of treatment. A subject, that is a patient, is effectively treated whenever a clinically beneficial result ensues. This may mean, for example, a complete resolution of the symptoms of a disease, a decrease in the severity of the symptoms of the disease, or a slowing of the disease's progression. These methods can further include the steps of a) identifying a subject (e.g., a patient and, more specifically, a human patient) who has colorectal neoplasia or colorectal cancer and b) providing to the subject an anticancer treatment, for example, a therapeutic agent, for example and immunotherapeutic agent, surgery, or radiation therapy. An amount of a therapeutic agent provided to the subject that results in a complete resolution of the symptoms of a disease, a decrease in the severity of the symptoms of the disease, or a slowing of the disease's progression is considered a therapeutically effective amount. The present methods may also include a monitoring step to help optimize dosing and scheduling as well as predict outcome. Monitoring can also be used to detect the onset of drug resistance, to rapidly distinguish responsive patients from nonresponsive patients or to assess recurrence of a cancer. Where there are signs of resistance or non-responsiveness, a clinician can choose an alternative or adjunctive agent before the tumor develops additional escape mechanisms.

The methods disclosed herein can also be used in combination with conventional methods for diagnosis and treatment of colorectal cancer. Thus, the diagnostic methods can be used along with standard diagnostic methods for colorectal cancer. For example, the methods can be used in combination with a fecal occult blood test, a fecal immunochemical test, or a colonoscopy. The methods can also be used with other colorectal cancer markers, for example, KRAS, NRAS, BRAF, CEA, CA 19-9, p53, MSL, DCC, MSI, and MMR.

The diagnostic methods disclosed herein can also be used in combination with colorectal cancer treatments. Colorectal cancer treatment methods fall into several general categories: surgery, chemotherapy, radiation therapy, targeted therapy and immunotherapy. Surgery can include colectomy, colostomy along with partial hepatectomy, or protectomy. Chemotherapy can be systemic chemotherapy or regional chemotherapy in which the chemotherapeutic agents are placed in direct proximity to an affected organ. Exemplary chemotherapeutic agents can include 5-fluorouracil, oxaliplatin or derivatives thereof, irinotecan or a derivative thereof, leucovorin, or capecitabine, mitomycin C, cisplatin, and doxorubicin. Radiation therapy can be external radiation therapy, using a machine to direct radiation toward the cancer or internal radiation therapy in which a radioactive substance is placed directly into or near the colorectal cancer. Targeted agents can include anti-angiogenic agents such as bevacizumab) or EGFR inhibitor monoclonal antibody (cetuximab, panitumumab), ramuciramab (anti-VEGFR2), aflibercept, regorafenib, tripfluridine-tipiracil or a combination thereof. Targeted agents can also be combined with standard chemotherapeutic agents. Immunotherapy can include administration of specific antibodies, for example anti-PD-1 antibodies, anti-PD-L-1 antibodies, and time-CTLA-4 antibodies, anti-CD 27 antibodies; cancer vaccines, adoptive cell therapy, oncolytic virus therapies, adjuvant immunotherapies, and cytokine-based therapies. Exemplary immunotherapeutics can include Keytruda, Opdiva, and iplimumab. Other treatment methods include stem cell transplantation, hyperthermia, photodynamic therapy, blood product donation and transfusion, or laser treatment.

We may use the terms "increased", "increase" or "up-regulated" to generally mean an increase in the level of a biomarker by a statistically significant amount. In some embodiments, an increase can be an increase of at least 10% as compared to a control, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a control, or at least about a 0.5-fold, or at least about a 1.0-fold, or at least about a 1.2-fold, or at least about a 1.5-fold, or at least about a 2-fold, or at least about a 3-fold, or at least about a 4-fold, or at least about a 5-fold or at least about a 10-fold increase, or any increase between 1.0-fold and 10-fold or greater as compared to a control.

We may use the terms "decrease", "decreased", "reduced", "reduction" or "down-regulated" to refer to a decrease in the level of a eukaryotic biomarker by a statistically significant amount. In some embodiments, a decrease can be a decrease of at least 10% as compared to a control, for example a decrease of at least about 20%, or at least about 30%, or at least about 40%, or at least about 50%, or at least about 60%, or at least about 70%, or at least about 80%, or at least about 90% or up to and including a 100% decrease (i.e. absent level as compared to a control), or any decrease between 10-100% as compared to a control, or at least about a 0.5-fold, or at least about a 1.0-fold, or at least about a 1.2-fold, or at least about a 1.5-fold, or at least about a 2-fold, or at least about a 3-fold, or at least about a 4-fold, or at least about a 5-fold or at least about a 10-fold decrease, or any decrease between 1.0-fold and 10-fold or greater as compared to a control.

The statistical significance of an increase in a eukaryotic biomarker or a decrease in a eukaryotic biomarker can be expressed as a p-value or a q-value. Depending upon the specific eukaryotic biomarker, p-value or q-value can be less than 0.05, less than 0.01, less than 0.005, less than 0.002, less than 0.001, or less than 0.0005. A q-value can be a derivative to a p-value. In some embodiments the q-value can be the p-value adjusted for the false discovery rate.

A control can be a biological sample obtained from a patient or a group of patients. In some embodiments, the control can be a reference value. A control can be obtained from an individual, or a population of individuals, who have been diagnosed as healthy. Healthy individuals can include, for example, individuals who have tested negative in a fecal parasitic test, a fecal bacteria test, a colonoscopy, or an endoscopy within the last year. A control can be obtained from an individual, or a population of individuals, who have been diagnosed as diseased. Diseased individuals can include, for example, individuals who have tested positive in a fecal parasitic test, a fecal bacterial test, a colonoscopy, or an endoscopy within the last year. A control can be obtained from an individual, or a population of individuals, who had previously been diagnosed with disease but are currently in remission, do not have active disease, or are not currently suffering from the disease. A control can be obtained from an individual at one, two, or more points in time. For example, a control can be a biological sample obtained from a subject at an earlier point in time. A control can be a standard reference value for a particular biomarker. A standard reference value can be derived based on evaluating individuals of similar age, sex, gender, body size, breed, ethnic background, or general health. In some embodiments, a control can be a value or values derived from an algorithm.

An experimental sample can be a biological sample obtained from a subject. An experimental sample can be obtained from a subject with known or unknown health status. In some embodiments, health status of a subject can be determined, for example, by analysis of an experimental sample, biopsy, physical examination, laboratory findings, visual inspection, or genetic analysis. The health status of a subject that can be determined via an experimental sample can be diseased, at risk for disease, or healthy.

Articles of Manufacture

Also provided are kits for detecting and quantifying selected stool-derived eukaryotic RNA biomarkers in a biological sample, for example, a stool sample. Accordingly, packaged products (e.g., sterile containers containing one or more of the compositions described herein and packaged for storage, shipment, or sale at concentrated or ready-to-use concentrations) and kits, are also within the scope of the invention. A product can include a container (e.g., a vial, jar, bottle, bag, microplate, microchip, or beads) containing one or more compositions of the invention. In addition, an article of manufacture further may include, for example, packaging materials, instructions for use, syringes, delivery devices, buffers, or other control reagents.

The kit can include a compound or agent capable of detecting RNA corresponding to 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers, for example, a stool-derived eukaryotic RNA biomarker selected from Table 1 or Table 2 or a combination of Table 1 and Table 2 or Table 3 or Table 4, in a biological sample; and a standard; and optionally one or more reagents necessary for performing detection, quantification, or amplification. In some embodiments, the kit can include a compound or agent capable of detecting RNA corresponding to 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers, for example, a stool-derived eukaryotic RNA biomarker selected from Table 1 or Table 2 or a combination of Table 1 and Table 2 or Table 3 or Table 4, in a biological sample; and a standard; and optionally one or more reagents necessary for performing detection, quantification, or amplification. The compounds, agents, and/or reagents can be packaged in a suitable container. The kit can further comprise instructions for using the kit to detect and quantify nucleic acid. The kit can also contain a control or a series of controls which can be assayed and compared to the test sample contained. Each component of the kit can be enclosed within an individual container and all of the various containers can be within a single package, along with instructions for interpreting the results of the assays performed using the kit. In some embodiments, the kits can include primers or oligonucleotide probes specific for one or more control markers. In some embodiments, the kits include reagents specific for the quantification of 2, 3, 4, 5, 6, 7, 8, 9, 10, 11, 12, 13, 14, 15, 16, 17, 18, 19, 20, 21, 22, 23, 24, 25, 26, 27, 28, 29, 30 or more stool-derived eukaryotic RNA biomarkers, for example, a stool-derived eukaryotic RNA biomarker selected from Table 1 or Table 2 or a combination of Table 1 and Table 2 or Table 3 or Table 4.

In some embodiments, the kit can include reagents specific for the separation of eukaryotic cells from bacterial cells and other stool components and extraction of stool-derived eukaryotic RNA from a patient's, for example, a human patient's, stool sample. Thus, the kit can include buffers, emulsion beads, silica beads, stabilization reagents, and various filters and containers for centrifugation. The kit can also include instructions for stool handling to minimize contamination of samples and to ensure stability of stool-derived eukaryotic RNA in the stool sample. The kit can also include items to ensure sample preservation, for example, stabilization buffers, coolants or heat packs. In some embodiments, the kit can include a stool collection device.

The product may also include a legend (e.g., a printed label or insert or other medium describing the product's use (e.g., an audio- or videotape or computer readable medium)). The legend can be associated with the container (e.g., affixed to the container) and can describe the manner in which the reagents can be used. The reagents can be ready for use (e.g., present in appropriate units), and may include one or more additional adjuvants, carriers, or other diluents. Alternatively, the reagents can be provided in a concentrated form with a diluent and instructions for dilution.

EXAMPLES

Example 1: Human Stool Sample Procurement

Human Stool Collection: Patients were asked to defecate into a bucket that fit over a toilet seat and the resulting samples were stored in a freezer until they were transported to the Kharkiv National Medical University (Kharkiv, Ukraine). The stool was aliquoted into 50 mL conical tubes and stored at −80° C. The samples were shipped from Kharkiv National Medical University on dry ice to Capital Biosciences (Gaithersburg, Md.) and immediately transferred to a −80° C. freezer. From there, the samples were shipped on dry ice to BioGenerator Labs (Saint Louis, Mo.) where they were stored in a −80° C. freezer until extraction.

Human Sample Types: Stool samples were obtained from 195 patients with colorectal cancer (stage I-IV), 126 patients with precancerous adenomas, 8 patients with benign polyps, and 125 patients with negative findings on a colonoscopy, resulting in 454 aggregate samples. Healthy individuals were patients with no history of colorectal cancer, inflammatory bowel disease, celiac disease, irritable bowel syndrome, diarrhea within the last 20 days or any other gastrointestinal disease. Benign polyp patients provided a stool sample prior to undergoing a colonoscopy where the physician detected a polyp that was deemed to be benign via a subsequent biopsy and histological evaluation. Diseased individuals were patients diagnosed with colorectal cancer or precancerous adenomas. Colorectal cancer patients had been diagnosed with stage I-stage IV colorectal cancer via colonoscopy and subsequent biopsy within the last month and had not yet received any post-biopsy treatment, which can include chemotherapy, radiation, and/or surgery. Precancerous adenoma patients provided a stool sample prior to undergoing a colonoscopy where the physician detected a polyp that was deemed to be precancerous via a subsequent biopsy and histological evaluation. The healthy and benign polyp individuals were matched with adenoma and cancer patients based on gender and age brackets (50-60 years, 60-70 years, 70-80 years and 80-90 years). The patients used for this collection were consented by Capital Biosciences. The Schulman Internal Review Board provided ethical oversight for this collection.

Example 2: Human Nucleic Acid Extraction

Total Nucleic Acid Extraction: Each stool sample was placed into a 50 mL conical tube. Approximately 1,000-25,000 mg of stool were added to each tube. An additional 20-40 mL of solution were added to each tube. This solution contained a mixture of Hanks Balanced Salt Solution (HBSS) (Sigma-Aldrich) with 0.05% Tween-20 (Sigma-Aldrich) and 0.0002% RNAse Inhibitor (Sigma-Aldrich). The stool was suspended into solution and rotated at approximately 0-10° C. for 0-10 minutes. The solution was centrifuged at 1000 rpm at 4° C. for 10 minutes and the supernatant was discarded. Approximately 4-10 mL of Easy-Mag® Lysis Buffer (bioMerieux) was added to the pellet and the pellet was re-suspended into solution. The solution was centrifuged at 2500-3500 rpm at 20-25° C. for 10-15 minutes. During the differential centrifugation, the solution separated into three layers. The bottom layer included solid cellular debris, the middle layer was a hydrophilic layer enriched for human nucleic acid and the top layer was a hydrophobic lipid layer. The top two layers were transferred to a new 15 mL conical tube and the solution was again centrifuged at 2500 rpm at 20-25° C. for 10 minutes. The result from this centrifugation step was separation into three layers: the bottom layer was solid cellular debris, the middle layer was a hydrophilic layer enriched for human nucleic acid, and the top layer was a hydrophobic lipid layer. To screen large debris from the solution, a 20 uL pipette tip was placed onto a 1 mL pipette tip and 2 mL of the hydrophilic layer was pipetted from the 15 mL tube and transferred to an EasyMag® Disposable cartridge (bioMerieux). Additionally, 60 uL of EasyMag® Magnetic Silica (bioMerieux) was added to the cartridge. The beads were mixed into the solution for 0.5-1 minute using a pipette. The nucleic acids, which were bound to the beads, were eluted into a buffer solution using the Specific A Protocol according to the manufacturer's directions. The volume of the eluted nucleic acids was 70 uL. This nucleic acid solution was pipetted into a 1.5 mL tube and placed on ice. The same EasyMag® Disposable cartridges (bioMerieux) that were used in the previous step were then reloaded with an additional 2 mL of the hydrophilic layer from the same solution in the 15 mL tube used previously using the same technique to screen out large debris. An additional 20 uL of EasyMag® Magnetic Silica (bioMerieux) was added to the cartridge. The beads were mixed into the solution for 0.5-1 minute using a pipette. As described above, the nucleic acids, which were bound to the beads, were eluted into a buffer solution using the Specific A Protocol according to the manufacturer's directions. The volume of the eluted nucleic acids was 70 uL. This nucleic acid solution was pipetted into the original 1.5 mL tube that already contained first 70 uL eluate and the combined solution was placed on ice.

DNAse Treatment: The 140 uL solution was treated with Baseline-Zero-DNase (Epicenter) at 35-40° C. for 20-40 minutes. A 1-2 mL aliquot of EasyMag® Lysis Buffer was added to the DNAse treated solution and the sample was transferred to a new EasyMag® Disposable cartridge. The entire solution was added to the new cartridge along with 60 uL of EasyMag® Magnetic Silica. The nucleic acids, which were bound to the beads, were eluted into a buffer solution using the EasyMag® Generic Protocol according to the manufacturer's directions. The volume of the eluted nucleic acids was 25 uL. This nucleic acid solution was pipetted into a 1.5 mL tube and stored at 0-6° C.

Example 3: Measurement of Human Nucleic Acid Levels in Human Stool Samples

Extraction Results: 1-2 uL of each of the samples extracted above was evaluated for total nucleic acid and RNA integrity using the Agilent 2100 Bioanalyzer. The samples were analyzed qualitatively and quantitatively. Electrophoretic analysis was used to check the quality of the extracted RNA. The electrophoresis file was read by comparing the bands for each sample to the bands represented by the size markers in the RNA ladder and identifying the 18S and 28S ribosomal RNA (rRNA) bands. The rRNA bands are the two large and prominent bands around the 2,000- nucleotide marker on the standardization ladder. Qualitatively, adequate banding and darker band intensities indicated that ample intact nucleic acid was available for further analysis such as microarray sequencing, polymerase chain reaction (PCR), nucleic acid sequencing, molecular barcoding, or probe-capture. The electropherogram is a graphical representation for each electrophoresis file with a quantification of the RNA Integrity Number (RIN), total RNA mass, and total rRNA mass. Quantitatively, the larger the RIN, the more total RNA mass, and the more total rRNA mass, the higher the likelihood a sample would be useful for further analysis such as microarray sequencing, polymerase chain reaction (PCR), nucleic acid sequencing, molecular barcoding, or probe-capture.

FIG. 1A is an electrophoresis file for six samples and an electropherogram for one sample that were extracted based on a method described in the literature. FIG. 1B is an electrophoresis file for six samples and an electropherogram for one sample that were extracted above. Samples extracted above resulted in larger RIN and more eukaryotic mass. The higher quality of the seRNA extracted above was also demonstrated by more distinct ribosomal RNA bands (18S and 28S) and less bacterial noise, as evidenced by minimal banding below the 18S band.

Example 4: seRNA Incubation in a Stabilization Buffer 11 samples were selected to undergo testing with a stabilization buffer. These samples were split into 5-gram aliquots, resulting in three cohorts: Cohort 1 (n=11), Cohort 2 (n=11) and Cohort 3 (n=8). Cohort 1 samples were extracted immediately using the method described above. (FIG. 2A). Cohort 2 samples were incubated in a stabilization buffer and stored at room temperature for 24 hours prior to extraction using the method described above (FIG. 2B). Cohort 3 samples were incubated in a stabilization buffer and stored at room temperature for 48 hours prior to extraction using the method described above (FIG. 2C).

Following extraction, all samples (n=30) were analyzed qualitatively using an Agilent Bioanalyzer. Clear and distinct intact ribosomal 18S and 28S bands are detected with isolated RNA from all samples. The intensity of the 18S and 28S, which can be used to estimate the amount of eukaryotic RNA, increased with incubation in a stabilization buffer. Further, bacterial noise, illustrated by banding below the 18S, decreased with incubation in a stabilization buffer.

Data from the Agilent Bioanalyzer also enabled quantification of the RNA integrity number (RIN) and eukaryotic mass. RIN was adequate for all samples. The overall RIN of each cohort increased with incubation in a stabilization buffer, with mean RINs of 4.6, 5.9, and 7.1 for Cohort 1, Cohort 2, and Cohort 3, respectively. Eukaryotic mass was adequate in all samples. The overall eukaryotic mass increased with incubation in a stabilization buffer, with mean masses of 11.1 ng, 39.7 ng, and 78.4 ng for Cohort 1, Cohort 2, and Cohort 3, respectively.

Example 5: Analysis of RNA Transcripts 330 samples were chosen for analysis using the Affymetrix GeneChip™ Human Transcriptome Array 2.0 (Santa Clara, Calif.). Approximately 100 ng of DNase-free fecal RNA was amplified with the Ambio WT-pico kit with subsequent hybridization to the Affymetrix GeneChip™ Human Transcriptome Array 2.0 as per the manufacturer's protocol. All samples were normalized using the Signal Space Transformation-Robust Multiarray Analysis (SST-RMA) with the Affymetrix Expression Console™.

Of the 70,523 transcript clusters in the Affymetrix Microarray, a subset of 5,149 transcript clusters that correspond to 3,977 genes were preselected to evaluate for differential expression. This initial selection reduced the false discovery rate and filtered out genes that have no known function in cancer development and progression.

The 330 individuals were split into a training set of 265 individuals and a testing set of 65 individuals. The training set was used to identify the differentially expressed genes and build a computational model, whereas the testing set was used to determine the detection accuracy of the computational model. The standard LIMMA package was used to identify a subset of RNA transcript clusters which were differentially expressed between individuals with either precancerous adenomas or CRC and individuals with no findings on a colonoscopy. All biomarkers were ranked according to the log odds scores and the 200 highest ranked biomarkers (p<0.05) served as the features in building the machine learning model. The Support Vector Machine Model (v-SVM) with RBF kernel was chosen for model development. The kernel function allows for the calculation of the distance between individuals by expanding the features into a higher dimensional space which is not explicitly computed. SVM finds the maximum margin hyperplane that separates the label groups. The parameter v defines the lower bound of the fraction of individuals that are used to determine the maximum margin. The SVM model was trained using expression levels for the 200 transcripts from all 265 individuals in the training set. Internal validation of the SVM attained a total ROC AUC of 0.776. The model attained a ROC AUC of 0.829 and 0.788 when evaluating CRC and adenomas, respectively (FIG. 3A).

This multi-target RNA biomarker algorithm was also used on the 65 individuals within the independent test set. The model correctly identified 79% (34 out of 43) of all individuals that had positive findings on a screening colonoscopy, 95% of individuals with precancerous adenomas and 65% of individuals with cancer. Model sensitivity for CRC was directly correlated with size such that 72% of tumors >4 cm in diameter were accurately detected. Model sensitivity for adenomas was agnostic to size, with 100% prediction accuracy for both small (<5 mm) and large (>1 cm) lesions (FIG. 3B).

Example 6: CRC Molecular Subtyping Using seRNA Expression Signatures

Of the 70,523 transcript clusters in the Affymetrix Microarray, a subset of transcript clusters that correspond to 274 genes was selected to annotate patient samples derived from individuals diagnosed with colorectal cancer with a consensus molecular subtype (CMS) of CRC defined by the Colorectal Cancer Subtyping Consortium (CRCSC) (FIG. 4A). The CRCSC classifier is organized based on the importance of each gene with regards to its ability to promote the accuracy of the molecular subtype classification. Transcript cluster expression was summarized at the gene level using the median luminescence for the transcript clusters associated with each gene. Gene expression data were normalized at the gene level and across the whole cohort using median expression levels. Normalized data were used as an input for the random forest classifier defined in the R Package CMS Classifier to label consensus molecular subtypes.

Figure 5:
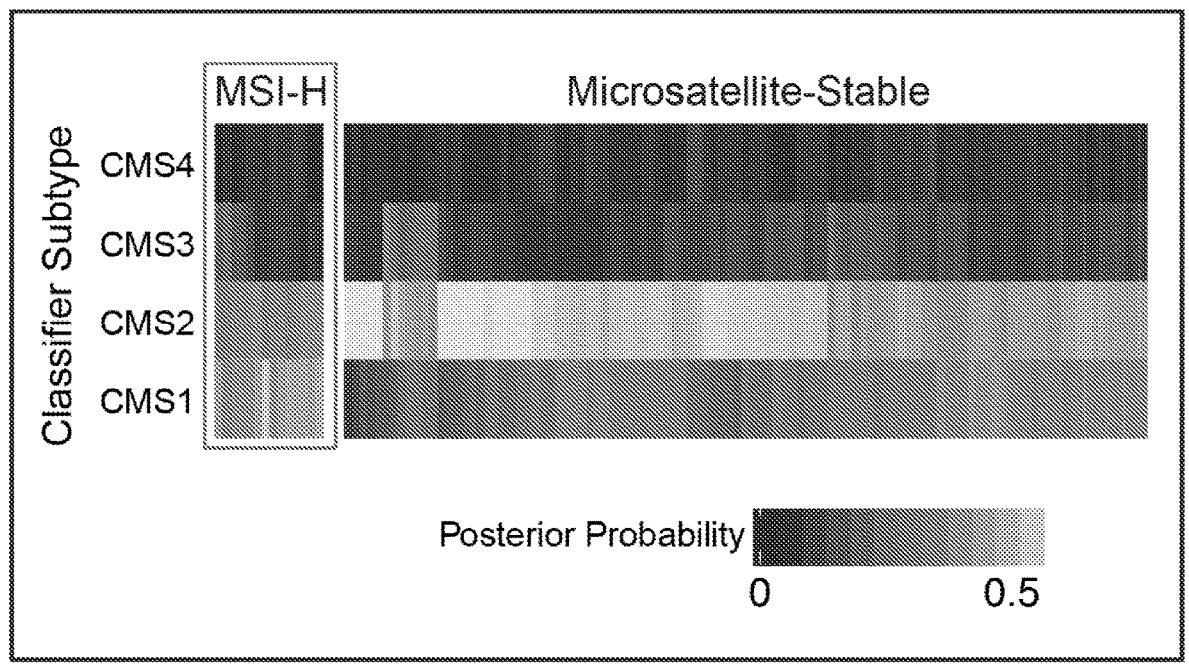
FIG. 5 is a heat map summarizing the stratification of patients by colorectal cancer CMS (consensus molecular subtype) using the Colorectal Cancer Subtyping Consortium classifier.

The output from the CMS Classifier includes four values, each is a posterior probability of how likely a sample is associated with CMS1-4. CMS1 comprises tumors with increased microsatellite instability (MSI-H) and signatures associated with immune infiltration. FIG. 4B provides 25 exemplary colorectal neoplasm molecular subtype biomarker genes useful for identification of colorectal cancer subtype CMS1. CMS2-4 are associated with canonical, metabolic, or mesenchymal gene expression signatures, respectively. Based on the CMS classifier, 14 out of 117 (12%) of individuals were classified as CMS1, 100 out of 117 (85%) were classified as CMS2-4 (canonical, metabolic, and mesenchymal), and 3 out of 117 (3%) were classified as mixed CMS1/CMS2 (FIG. 5).

Example 7: Human Stool Sample Procurement, Extraction & Measurement

Human Stool Collection: Patients were asked to defecate into a bucket that fit over a toilet seat and the resulting samples were picked up by a courier and transported to the Digestive Diseases Research Core Center at the Washington University School of Medicine (Saint Louis, Mo.). The stool was aliquoted into 50 mL conical tubes and stored at −80° C. From there, the samples were transported on dry ice to BioGenerator Labs (Saint Louis, Mo.) where they were stored in a −80° C. freezer until extraction. The patients used for this collection were consented by the Washington University School of Medicine. Washington University School of Medicine Internal Review Board also provided ethical oversight for this collection.

Human Sample Types: Stool samples were obtained from 6 patients with colorectal cancer (stage I-IV), 4 patients with pre-cancerous adenomas, and 14 patients with negative findings on a colonoscopy, resulting in 24 aggregate samples. These samples were derived from Human Stool Collection at both Kharkiv National Medical University and Washington University School of Medicine. The sample labels were identified and matched in a manner consistent with criteria outlined previously from Human Sample Types.

Total Nucleic Acid Extraction: seRNA was extracted from the samples in a manner consistent with methods outlined previously for Total Nucleic Acid Extraction, including DNAse Treatment, and the quality of the seRNA was analyzed in a manner consistent with methods outlined in Extraction Results.

Example 8: Analysis of RNA Transcripts

Library Preparation: Libraries of the seRNA were generated using an Illumina Targeted RNA Custom Panel that consisted of 398 custom amplicons. Library preparation relied on the steps of initial synthesis of cDNA using ProtoScript II Reverse Transcriptase (Illumina), hybridization of the oligo pool to the targeted seRNA, extension of the oligos using Illumina reagents (AM1, ELM4, RSB, UB1), and amplification through polymerase chain reaction (PCR). Total mass input ranged from 200-400 ng and the number of PCR cycles used ranged from 26-28x. After library amplification, the cDNA capture was cleaned using Illumina reagents (RSB, AMPure, XP bead EtOh). Library preparations were analyzed for quantity and quality using Agilent BioAnalyzer and Qubit Fluorometric Quantitation (Thermo Fisher). All samples described in this analysis passed initial quality check and were eligible for next-generation sequencing.

Sequencing: Unique indices were used for individual samples to allow for pooling of library preparations and multiplexing of all samples into the same flow cell on an Illumina NextSeq System. All 24 samples were pooled across one lane in a mid-output flow cell (Illumina). The first 150 base-pairs on each end of a read were sequenced (2×150) and sequenced reads were appended to output FASTQ files. Quality check of the FASTQ files showed that 19 samples had adequate total reads and adequate quality for bioinformatic analysis.

Alignment: After sequencing, custom primer sequences were trimmed from the sequence and trimmed reads were aligned to the most current reference genome (GRCh38). Transcript expression was obtained by calculating the average coverage across loci. Transcript expressions were normalized by average coverage for two housekeeping genes (GAPDH and ACTB).

Example 9: Biological Replicates on Various Platforms

Figure 6:
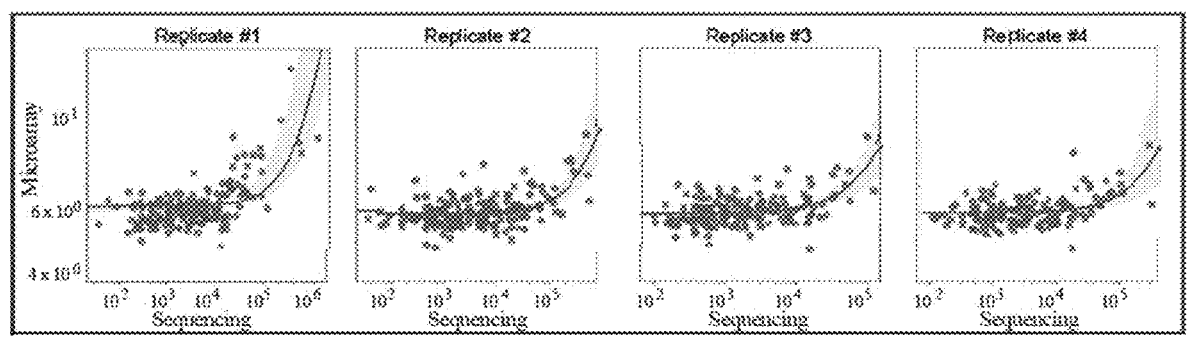
FIG. 6 depicts the correlation of 4 pairs of biological replicates when comparing transcript expression of 398 genes as measured by Affymetrix Human Transcriptome Array 2.0 and Illumina Targeted RNA Custom Panel.

Four samples were evaluated on both microarray and sequencing. Linear regression of 398 transcripts across platforms showed moderate reproducibility (Pearson's r range=0.48-0.63). Sequencing showed increased resolution relative to microarray as evidenced by range of signal for transcripts with low luminescence (FIG. 6).

Example 10: Hierarchical Clustering Analysis Using seRNA

Figure 7:
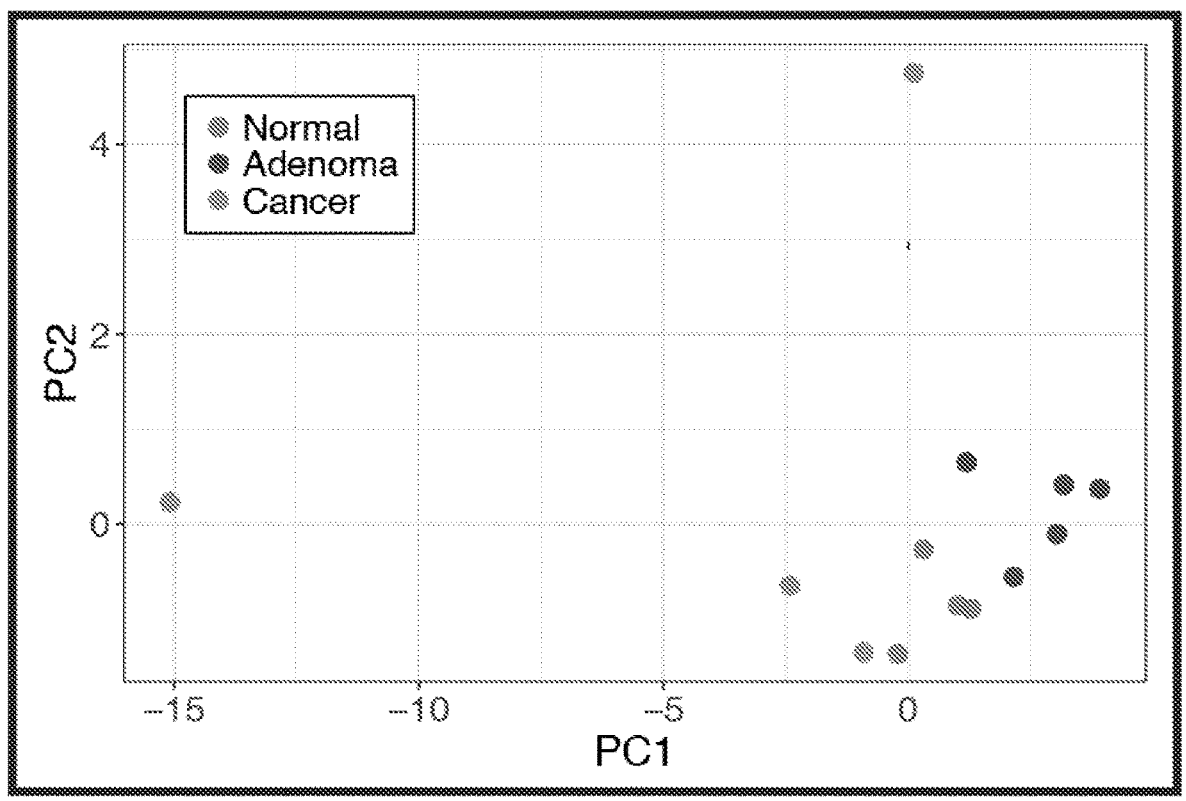
FIG. 7 is a principal component analysis graph depicting hierarchical clustering of 13 patients with colorectal cancer, adenomas, and no neoplastic findings.

Unsupervised principal component analysis (PCA) was performed on RNA sequencing data for all 13 unique samples. Clustering was observed amongst patients with CRC, patients with adenomas, and patients with no neoplastic findings. Samples from patients with cancer demonstrated the largest variation and separation from other patient populations, whereas samples from patients with no neoplastic findings demonstrated more narrow clustering (FIG. 7).

Example 11: Evaluation of Sequencing Variants Using seRNA

Figure 8:
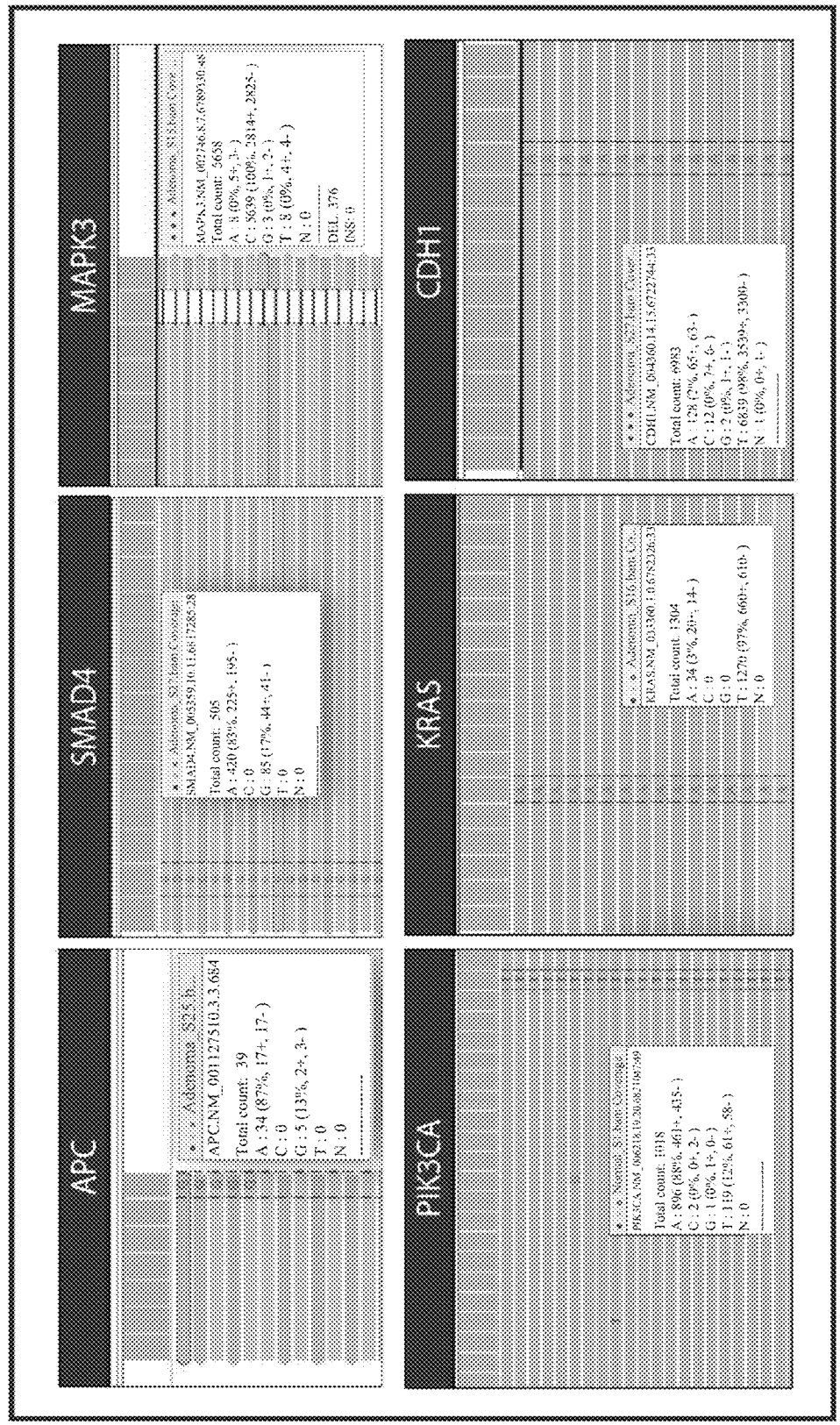
FIG. 8 depicts six putative somatic variants identified in stool samples derived from human subjects diagnosed with adenomas and colorectal cancer.

Variant Calling & Annotation: Integrative Genomics Viewer was used to identify variants implicated in CRC tumorigenesis. The amplicon panel covered about 3% of the genomic space for the 398 captured genes. Exemplary driver mutations are shown in FIG. 9. As shown in FIG. 8, we identified several potential driver mutations. These mutations included a missense mutation in APC (13% Variant Allele Frequency (VAF)) in a patient with high risk adenomas, a missense mutation in SMAD4 (17% VAF) in a patient with high risk adenomas, a 3' deletion in the regulatory region of MAPK3 (7% VAF) in a patient with stage I CRC, a missense mutation in PIK3CA (12% VAF) in a patient with no findings on a colonoscopy, a missense mutation in KRAS (3% VAF) in a patient with high risk adenomas, and a missense mutation in CDH1 (2% VAF) in a patient with high risk adenomas (FIG. 8).

Example 12: Human Stool Sample Procurement

Human Stool Collection: Stool samples were obtained by the Digestive Disease Research Core Center (DDRCC) at the Washington University School of Medicine (St. Louis, Mo.). All patients were sent a stool sample collection kit by mail and returned the kit via courier to the DDRCC. Clinical data (e.g., demographic information, colonoscopy results, etc.) were collected by the DDRCC. Each sample was tested for blood in the stool using a commercially available fecal immunochemical test (FIT) (Polymedco, OC-Light S FIT) prior to being frozen at −80° C. Each patient recruited for the study had a colonoscopy performed and those with positive findings underwent biopsy and subsequent histopathologic review to determine neoplastic classification. Adenoma classification was stratified based on histopathology (benign vs. precancerous), number of polyps, size of polyps, and differentiation. Cancer classification was stratified based on the American Joint Committee on Cancer (AJCC) 7 TNM system. If the patient had no findings during the colonoscopy, he or she was labeled as healthy.

Human Sample Types: In total, stool samples from 275 individuals were collected for this study. Sequencing data, a FIT, demographic information (i.e., gender, age, ethnicity, smoking status, and family history), and colonoscopy results with histopathology information, if applicable, were obtained for all patients. In the study, 11 patients had CRC (stage I-IV), 26 patients had high-risk adenomas (HRAs), 37 patients had medium-risk adenomas (MRAs), 61 patients had low-risk adenomas (LRAs), 50 patients had benign polyps, and 90 patients had no findings on a colonoscopy. Patient type, demographics, and processing information are summarized in FIG. 10. Healthy individuals were patients with no findings on a colonoscopy and no history of colorectal cancer, inflammatory bowel disease, celiac disease, irritable bowel syndrome, diarrhea within the last 20 days or any other gastrointestinal disease. Benign polyp patients provided a stool sample prior to undergoing a colonoscopy where the physician detected a polyp that was deemed to be benign via a subsequent biopsy and histological evaluation. Diseased individuals were patients diagnosed with colorectal cancer or precancerous adenomas. Colorectal cancer patients had been diagnosed with stage I-stage IV colorectal cancer via colonoscopy and subsequent biopsy within the last month and had not yet received any post-biopsy treatment, which can include chemotherapy, radiation, and/or surgery. Precancerous adenoma patients (HRAs, MRAs, and LRAs) provided a stool sample prior to undergoing a colonoscopy where the physician detected a polyp that was deemed to be precancerous via a subsequent biopsy and histological evaluation. Stratification of adenoma risk was based on size of the polyp, number of polyps, extent of dysplasia, and cellular morphology. The patient population was enriched for colorectal cancer patients, but the remainder of the samples were representative of an asymptomatic screening population. The patients used for this collection were consented by the Washington University School of Medicine. The Washington University School of Medicine Internal Review Board provided ethical oversight for this collection (IRB #20111107).

Separation into Training & Testing Sets: 154 prospectively collected stool samples were used as a training set and 110 prospectively collected stool samples were used as a hold-out test set. 11 retrospectively collected stool samples from CRC patients were also included in the hold out test set. The training set and hold out test set were evaluated for categorical, demographic, and handling differences using a t-test (population means) or z-test (population frequencies), and significance was indicated if the p-value was less than 0.05. There were two statistically significant differences between the characteristics of the training set and the hold out test set. First, retrospectively collected samples (i.e., samples from patients with CRC) were not included in the training set. Second, the hold out test set had different processing quality relative to the training set. Specifically, there was a reduction in the average stool input used for stool-derived eukaryotic RNA extraction (12.9 grams vs. 12.0 grams; p-value=0.03), there was a reduction in the average stool-derived eukaryotic RNA concentration (168.6 ng/uL vs. 56.1 ng/uL; p-value <0.01), and there was a reduction in average library preparation fragment size (200.6 base pairs vs. 192.2 base pairs; p-value <0.01) (FIG. 10).

Example 13: Development of a Custom Capture Panel

Panel Transcripts: A custom capture panel of 639 amplicons was developed for library preparation in the Illumina DesignStudio. The custom capture probes were associated with 408 transcripts, which were selected using previously conducted research and the literature.

Microarray Transcripts: Transcripts were selected based on a microarray experiment. For this experiment, total seRNA was extracted from stool samples and expression was assessed using the Affymetrix Human Transcriptome Array 2.0 (Thermo Fisher Scientific, Waltham, Mass.). Microarray expression profiles derived from 177 patients with CRC or precancerous adenomas (diseased cohort) were compared to expression profiles from 88 patients with no findings on a colonoscopy (healthy cohort). 214 transcripts were identified as being differential expressed (p<0.03) and were selected for the capture panel.

NanoString Transcripts: Transcripts were selected based on a NanoString experiment. For this experiment, total seRNA was extracted from stool samples and expression was assessed using the nCounter® PanCancer Pathways Panel (NanoString, Seattle, Wash.) and the nCounter® PanCancer Progression Panel (NanoString, Seattle, Wash.). NanoString expression profiles derived from 59 patients with CRC or precancerous adenomas (diseased cohort) were compared to expression profiles from 26 patients with no findings on a colonoscopy (healthy cohort). 123 transcripts were identified as being differentially expressed and were selected for the capture panel.

Other Transcripts: The literature was evaluated for additional transcripts implicated in CRC. This included searching GeneCards, ClinVar, Catalogue of Somatic Mutations in Cancer (COSMIC), Clinical Interpretations of Variants in Cancer (CIViC), the Colorectal Cancer Subtyping Consortium classifier, and other pertinent studies. 71 transcripts were selected for the custom capture panel using these literatures.

Example 14: Human Nucleic Acid Extraction

Total Nucleic Acid Extraction: Each stool sample was placed into a 50 mL conical tube. Approximately 6,000-25,000 mg of stool was added to each tube. An additional 20-40 mL of solution was added to each tube. This solution contained a mixture of 10 mM Trizma base (Sigma-Aldrich, St. Louis, Mo.), 1 mM EDTA (Sigma Aldrich) with 0.05% Tween-20 (Sigma-Aldrich) and 0.0002% RNase Inhibitor (Sigma-Aldrich) at pH 7.5. The solution was centrifuged at 1000 rpm at 4° C. for 10 minutes and the supernatant was discarded. Approximately 4-10 mL of EasyMag® Lysis Buffer (bioMérieux, Durham, N.C.) was added to the pellet and the pellet was re-suspended into solution. The solution was centrifuged at 2500-3500 rpm at 20-25° C. for 10-15 minutes. During the differential centrifugation, the solution separated into three layers. The bottom layer included solid cellular debris, the middle layer was a hydrophilic layer enriched for human nucleic acid, and the top layer was a hydrophobic lipid layer. The top two layers were transferred to a new 15 mL conical tube and the solution was again centrifuged at 2500 rpm at 20-25° C. for 15 minutes. The result from this centrifugation step was separation into three layers: the bottom layer was solid cellular debris, the middle layer was a hydrophilic layer enriched for human nucleic acid, and the top layer was a hydrophobic lipid layer. To screen large debris from the solution, a 10 uL pipette tip was placed onto a 1 mL pipette tip and 2 mL of the hydrophilic layer was pipetted from the 15 mL tube and transferred to an EasyMag® Disposable cartridge (bioMerieux). Additionally, 50 uL of EasyMag® Magnetic Silica (bioMerieux) was added to the cartridge. The beads were mixed into the solution for 0.5-1 minute using a pipette. The nucleic acids, which were bound to the beads, were eluted into a buffer solution using the Specific A Protocol according to the manufacturer's directions. The volume of the eluted nucleic acids was 70 uL. This nucleic acid solution was pipetted into a 1.5 mL tube and placed on ice. The same EasyMag® Disposable cartridges (bioMerieux) that were used in the previous step were then reloaded with an additional 2 mL of the hydrophilic layer from the same solution in the 15 mL tube used previously using the same technique to screen out large debris. An additional 20 uL of EasyMag® Magnetic Silica (bioMerieux) was added to the cartridge. The beads were mixed into the solution for 0.5-1 minute using a pipette. As described above, the nucleic acids, which were bound to the beads, were eluted into a buffer solution using the Specific A Protocol according to the manufacturer's directions. The volume of the eluted nucleic acids was 70 uL. This nucleic acid solution was pipetted into the original 1.5 mL tube that already contained first 70 uL eluate and the combined solution was placed on ice. An additional 2 mL of the hydrophilic layer from the same 15 mL solution previously used was added to a new EasyMag® Disposable cartridge (bioMerieux) using the same technique to screen out large debris. Additionally, 20 uL of EasyMag® Magnetic Silica (bioMerieux) was added to the cartridge. The beads were mixed into the solution for 0.5-1 minute using a pipette. The nucleic acids, which were bound to the beads, were eluted into a buffer solution using the Specific A Protocol according to the manufacturer's directions. The volume of the eluted nucleic acids was 70 uL. This nucleic acid solution was pipetted into the 1.5 mL tube containing the first two eluates and the combined solution was placed on ice. The same EasyMag® Disposable cartridges (bioMerieux) that were used in the previous step were then reloaded with an additional 2 mL of the hydrophilic layer from the same solution in the 15 mL tube used previously using the same technique to screen out large debris. An additional 20 uL of EasyMag® Magnetic Silica (bioMerieux) was added to the cartridge. The beads were mixed into the solution for 0.5-1 minute using a pipette. As described above, the nucleic acids, which were bound to the beads, were eluted into a buffer solution using the Specific A Protocol according to the manufacturer's directions. The volume of the eluted nucleic acids was 70 uL. This nucleic acid solution was pipetted into the original 1.5 mL tube that already contained the first three 70 uL eluates and the combined solution was placed on ice.

DNase Treatment: The 280 uL solution was treated with Baseline-Zero-DNase (Epicenter) at 35-40° C. for 20-40 minutes. A 1-2 mL aliquot of EasyMag® Lysis Buffer was added to the DNase treated solution and the sample was transferred to a new EasyMag® Disposable cartridge. The entire solution was added to the new cartridge along with 85 uL of EasyMag® Magnetic Silica. The nucleic acids, which were bound to the beads, were eluted into a buffer solution using the EasyMag® Generic Protocol according to the manufacturer's directions. The volume of the eluted nucleic acids was 25 uL. This nucleic acid solution was pipetted into a 1.5 mL tube and stored at −80° C.

Example 15: Measurement of Human Nucleic Acid Levels in Human Stool Samples

Extraction Results: 1-2 uL of each of the samples extracted above was evaluated for total nucleic acid and RNA integrity using the Agilent 2100 Bioanalyzer. The samples were analyzed qualitatively and quantitatively. Electrophoretic analysis was used to check the quality of the extracted RNA. The electrophoresis file was read by comparing the bands for each sample to the bands represented by the size markers in the RNA ladder and identifying the 18S and 28S ribosomal RNA (rRNA) bands. The rRNA bands are the two large and prominent bands around the 2,000-nucleotide marker on the standardization ladder. Qualitatively, adequate banding and darker band intensities indicated that ample intact nucleic acid was available for further analysis such as microarray sequencing, polymerase chain reaction (PCR), nucleic acid sequencing, molecular barcoding, amplicon sequencing, or probe-capture. The electropherogram is a graphical representation for each electrophoresis file with a quantification of the RNA Integrity Number (RIN), total RNA mass, and total rRNA mass. Quantitatively, the larger the RIN, the more total RNA mass, and the more total rRNA mass, the higher the likelihood a sample would be useful for further analysis such as microarray sequencing, polymerase chain reaction (PCR), nucleic acid sequencing, molecular barcoding, amplicon sequencing, or probe-capture. Samples were also evaluated for RNA concentration using the Qubit 4.0 Fluorometer. RNA concentration is determined by quantification of fluorescence generated by Qubit assay components, which selectively bind to RNA present in eluates. Quantitatively, the higher the RNA concentration, the higher the likelihood a sample would be useful for further analysis such as microarray sequencing, polymerase chain reaction (PCR), nucleic acid sequencing, molecular barcoding, amplicon sequencing, or probe-capture.

Example 16: Analysis of RNA Transcripts

Library Preparation: Libraries of the seRNA were generated using an Illumina Targeted RNA Custom Panel that consisted of 639 custom amplicons. Library preparation relied on the steps of initial synthesis of cDNA using ProtoScript II Reverse Transcriptase (Illumina, San Diego, Calif.), hybridization of the oligo pool to the targeted seRNA, extension of the oligos using Illumina reagents (AM1, ELM4, RSB, UB1), and amplification through polymerase chain reaction (PCR). Total mass input ranged from 200-400 ng and the number of PCR cycles used ranged from 28×-30×. After library amplification, the cDNA capture was cleaned using Illumina reagents (RSB, AMPure, XP bead EtOH). Library preparations were analyzed for quantity and quality using the Agilent 2100 BioAnalyzer and the Qubit 4.0 Fluorometer (Thermo Fisher). All samples described in this analysis passed initial quality check and were eligible for downstream analysis.

Sequencing Analysis: Unique indices were used for individual samples to allow for pooling of library preparations and multiplexing of samples into flow cells on an Illumina NextSeq 550 System. A PhiX spike-in was used for quality control. The 275 samples were pooled across 8 individual high-output flow cell runs (Illumina). Up to 150 base-pairs on each end of a read were sequenced (2×150) and sequenced reads were appended to output FASTQ files. Quality check of the FASTQ files showed that all 275 samples had adequate total reads (>100,000) and adequate quality for bioinformatic analysis.

Alignment: After sequencing, custom primer sequences were trimmed from the read and aligned to the most current reference genome (GRCh38) via HISAT2.3.0. Transcript expression was obtained by calculating the average coverage across loci. For each transcript, raw amplicon expression was normalized to GAPDH, an internal housekeeping gene, such that reported expression equates to amplicon read count per million mapped-GAPDH reads.

Figure 11A:
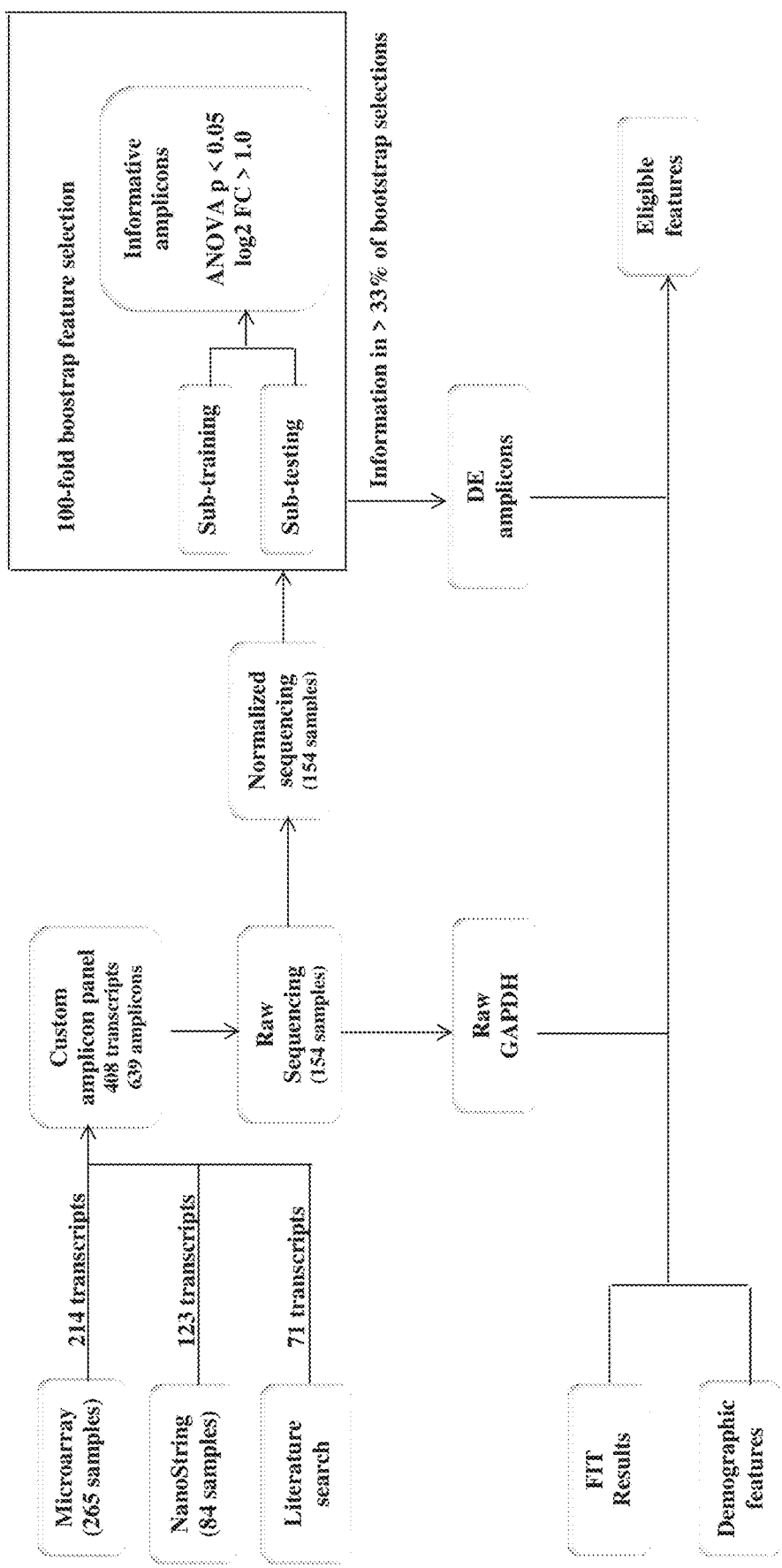
FIG. 11A is a flow chart of the eligible feature selection using bootstrapping of the testing set.
Figure 11B:
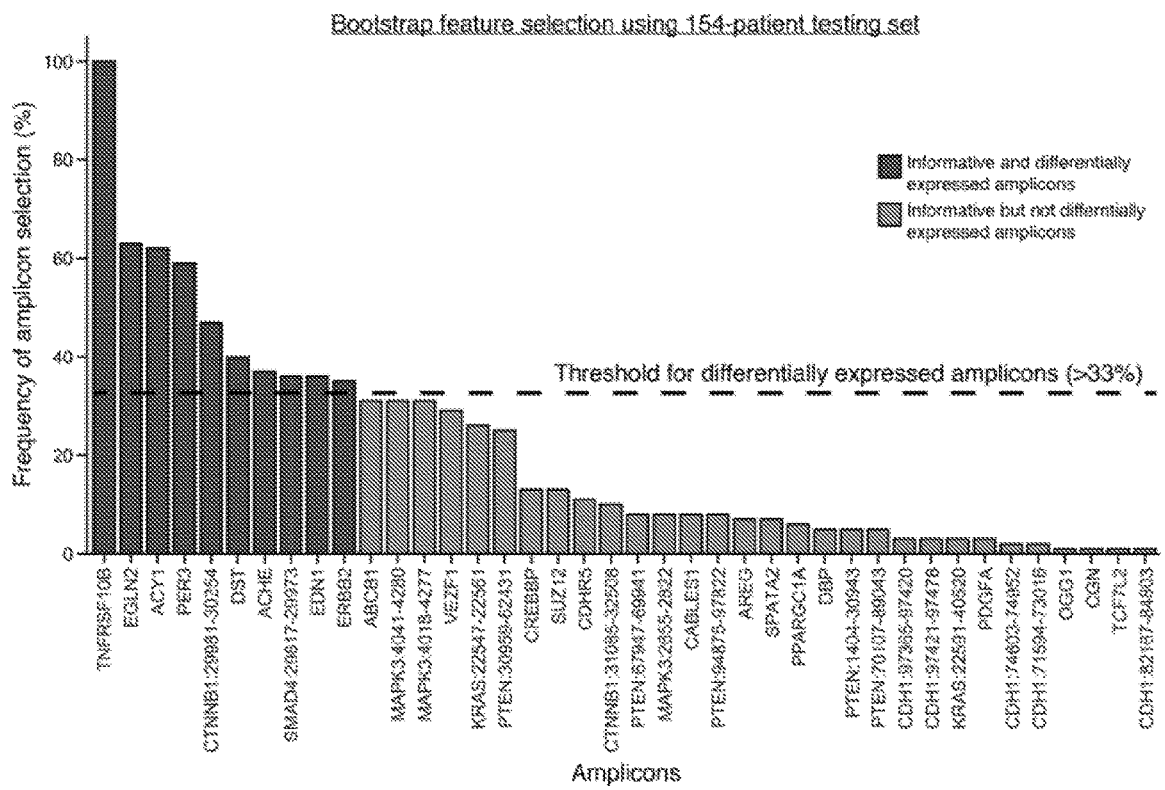
FIG. 11B is a graph of the eligible features selected.
Figure 12:
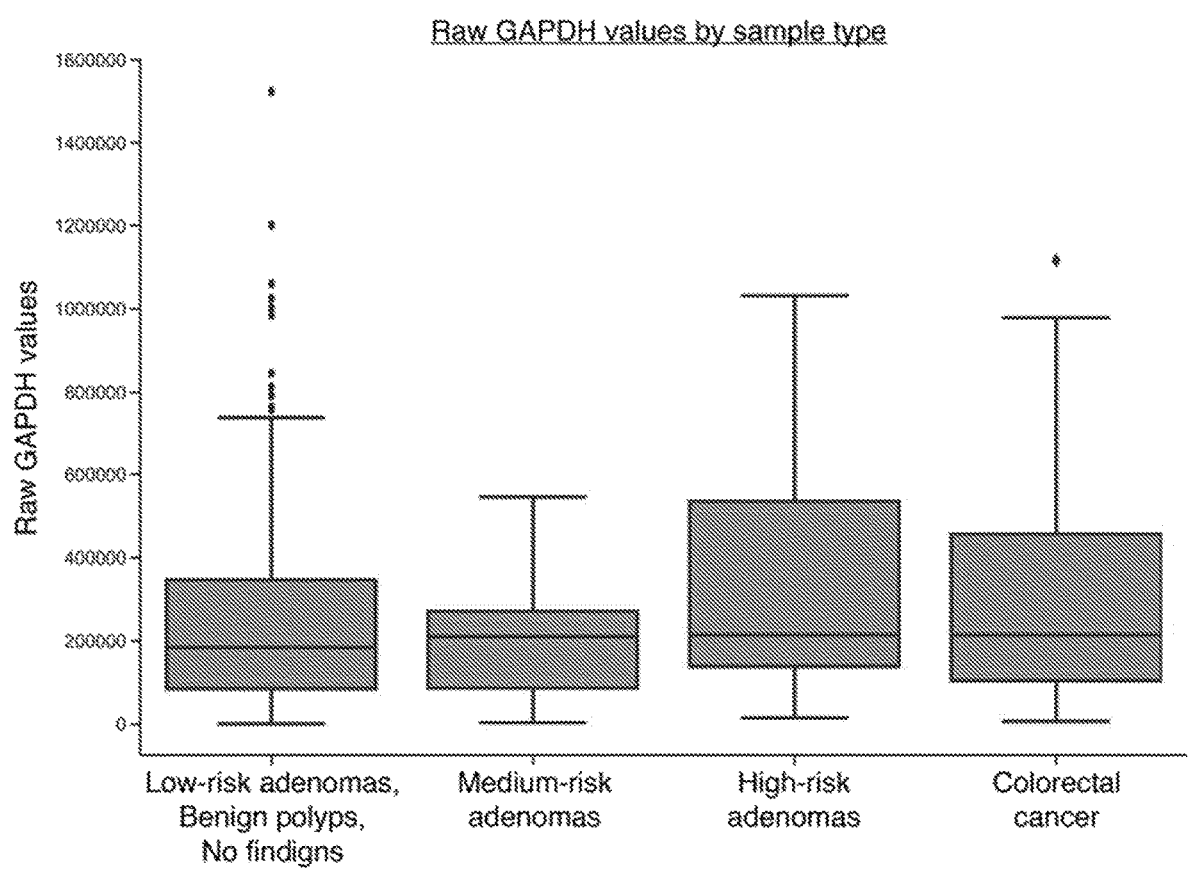
FIG. 12 is a graph of Raw GAPDH values for patients with no findings on a colonoscopy, benign polyps, low-risk adenomas, medium-risk adenomas, high-risk adenomas, and colorectal cancer.

Transcript Selection: Normalized expression of 639 amplicons was evaluated for all samples in the training set (n=154 samples). Of these 639 amplicons, 48 amplicons were not expressed in any sample and an additional 71 amplicons were not expressed in >95% of all samples; these amplicons were eliminated from the analysis. For the remaining amplicons, a bootstrap analysis was performed by splitting the training set into 100 different 9:1 splits, whereby each split was assessed for informative amplicons. An amplicon was considered informative if the absolute $\log_2$ fold-change was greater than 1 in both contrast groups (HRAs vs. LRAs, benign polyps, no findings on colonoscopy; MRAs vs. LRAs, benign polyps, no findings on colonoscopy) and the ANOVA between the contrast groups had a p-value <0.05. The transcript selection process is further illustrated in FIG. 11A. In total, there were 40 amplicons from 29 genes identified as informative in at least 1 of the 100 splits (FIG. 11B). If an amplicon was deemed informative in at least 33% of all bootstrapped splits, it was considered differentially expressed and eligible as a feature for model development. There were 10 amplicons identified as differentially expressed (informative in at least 33 of the 100 splits) (FIG. 11B). Raw GAPDH values are considered a measure for total eukaryotic RNA in each sample. It was observed that raw GAPDH values were elevated in patients with MRAs, HRAs, and CRC, relative to healthy patients (FIG. 12). Demographic features (age, smoking status, previous family history, ethnicity, and gender) were also considered for model development. Ultimately, the 10 differentially expressed transcripts, raw GAPDH values, and 2 demographic identifiers (age and smoking status) were eligible as features for model development.

Example 17: Random Forest Model Development

A random forest model was built using the 154-patient training set and all 13 eligible features. 5,000 decision trees were constructed from bootstrapped training samples; each node split was optimized by Gini Importance; each tree was built until it reached full depth. Although specific embodiments are discussed herein, it will be appreciated that any suitable model, such as a random forest model using a greater and/or lesser number of decision trees, a greater and/or lesser number of eligible features, etc. may be generated. Additionally, other types of models, such as a deep learning model or a support vector model might be used with varied parameters. The random forest model used eligible features, such as differentially expressed transcripts, raw GAPDH values, age, and smoking status. Although specific embodiments are discussed herein, it will be appreciated that any suitable model, such as a random forest model using all of the informative features and/or a selected subset of the informative features, may be generated.

Figure 13A:
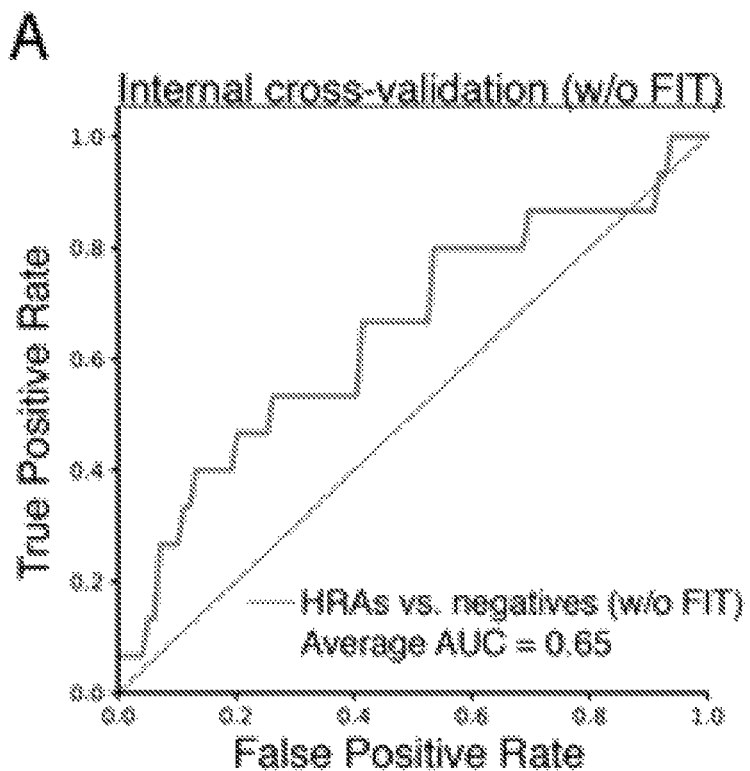
FIGS. 13A-13B are graphs showing model performance for detection of high-risk adenomas (HRAs) based on internal cross-validation (n=154 patients).
Figure 13B:
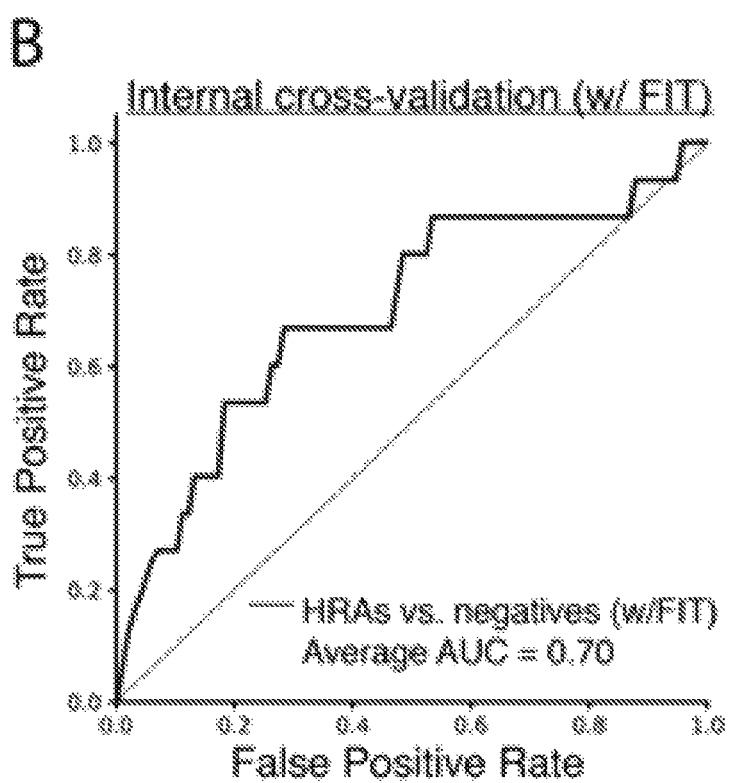

Output from the model was configured to provide a prediction between 0-1 whereby a larger number reflects increased confidence in a neoplastic or positive finding. A fecal immunochemical test (FIT) was used in some embodiments to alter confidence in a neoplastic or positive finding. For example, for a FIT positive sample, the prediction score would increase to 1. 3-fold internal cross-validation was used to assess training model performance. 3-fold internal cross-validation used 3 different 2:1 splits whereby a model was built using the larger split and employed on the smaller split. Receiver operating characteristic (ROC) curves were created using model predictions and area under the curve (AUC) was used to measure model performance. The median ROC curve from the 3 splits was used to approximate cross-validation performance. ROC curves were plotted with and without incorporating the FIT feature. For ROC curves plotted with the FIT feature, a positive FIT forced model prediction to equal 1. In the provided example, internal cross-validation without the FIT feature yielded a ROC AUC of 0.65 for HRAs versus all other categories (MRAs, LRAs, benign polyps, and no findings on a colonoscopy). In the provided example, internal cross-validation with the FIT feature yielded a ROC AUC of 0.70 for HRAs versus all other categories (MRAs, LRAs, benign polyps, and no findings on a colonoscopy) (FIGS. 13A-13B).

Hold Out Test Set: A final random forest model was built using all 154 samples within the training set. For the generated model, the most influential features as measured by Gini Importance were ACY1 and TNFRSF10B (Gini Importance >0.13) and the least important feature was PER3 (Gini Importance <0.05). Raw GAPDH values were the 4th most important feature in building the random forest model (FIG. 14). This model was employed on the 110 prospectively collected stool samples in the hold out test set. ROC curves were plotted with and without the FIT feature and area under the curve (AUC) was used to measure model performance. The model attained a ROC AUC of 0.67 without the FIT feature and a ROC AUC of 0.78 with the FIT feature (FIGS. 15A-15B).

Figures 16A, 16B:
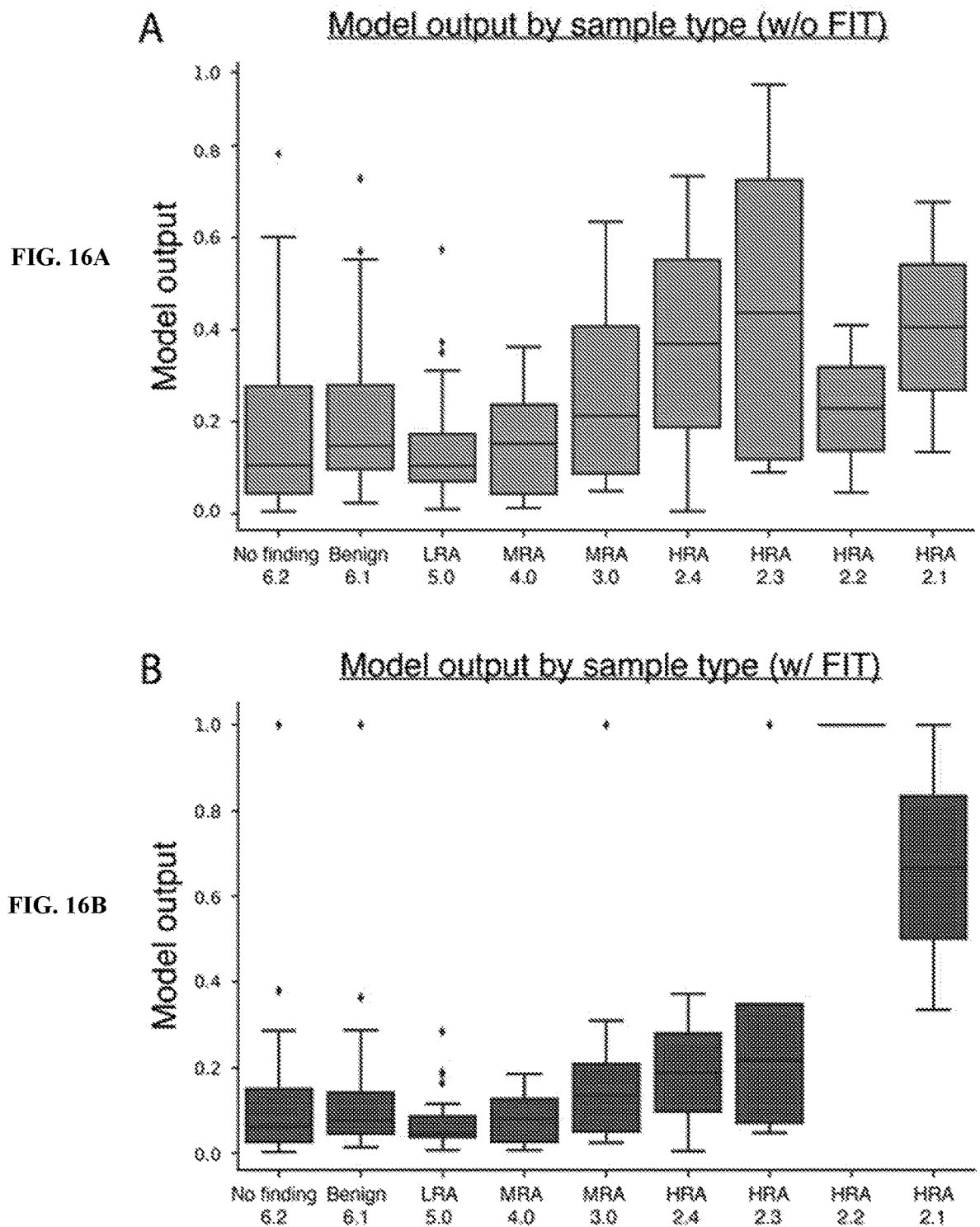
FIG. 16A is a graph showing model predictions sorted by disease severity without the fecal immunochemical test (FIT) feature.
FIG. 16B is a graph showing model predictions sorted by disease severity with the fecal immunochemical test (FIT) feature.

Model Predictions: Model predictions in the hold out test set were correlated with disease severity (FIGS. 16A-16B). The model output correlation with disease severity was a direct reflection of the biology and not specifically trained as part of the model. In the foregoing embodiment, feature selection and model input included the use of three categories (HRAs, MRAs, and all others) however, disease subtypes (e.g., subsets of HRAs) and disease order (e.g., HRAs are more severe than MRAs) were not used as features for model training. Given that model output is correlated to disease severity, this permits prospective identification of specific subtypes and severity of disease using model output. Further, altering model parameters to provide model with disease severity information improved stratification of positive and negative findings.

Figure 17A:
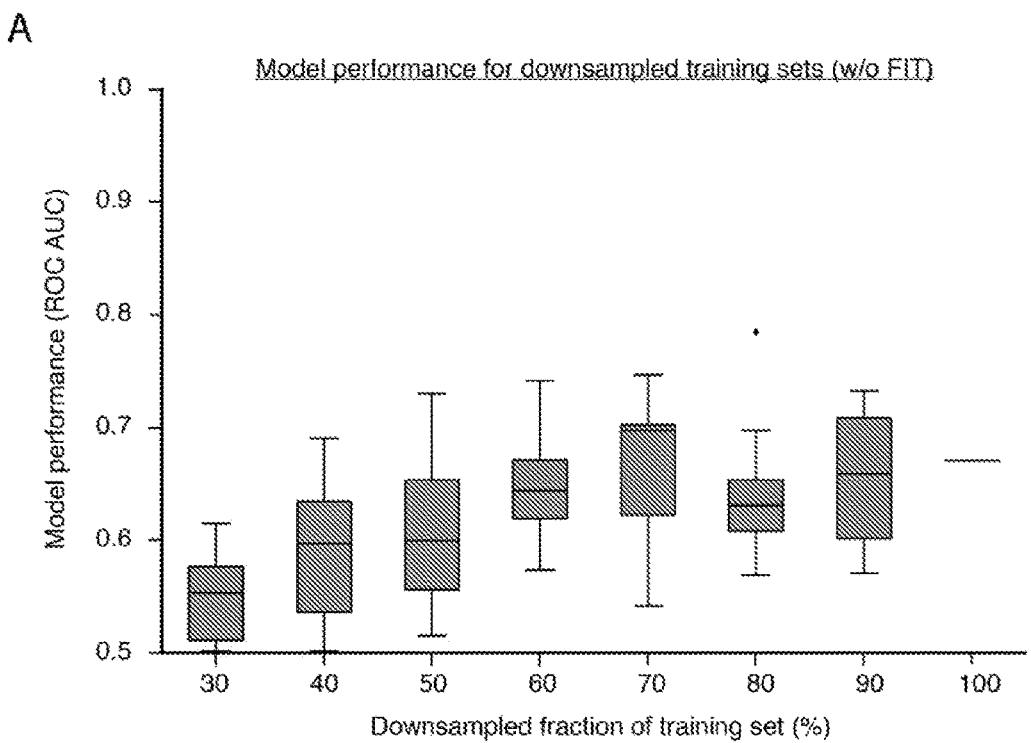
FIG. 17A is a graph showing results of an incremental downsampling analysis without the fecal immunochemical test (FIT) feature.
Figure 17B:
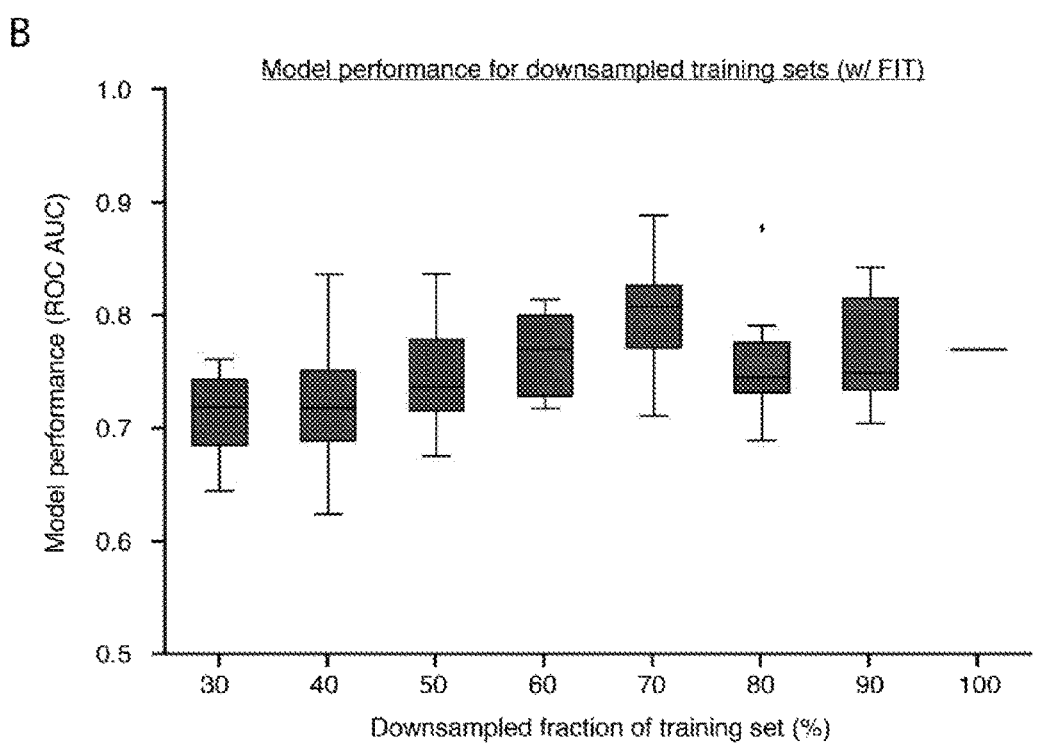
FIG. 17B is a graph showing results of an incremental downsampling analysis with the fecal immunochemical test (FIT) feature.

Downsampling Analysis: To understand the extent of model training, downsampling fractions of the 154 samples in the training set were selected and performance was assessed using the hold out test set. The downsampling fractions ranged from 30% to 100% with 10% increments. For each downsampling fraction, feature selection was performed using bootstrapping, a random forest model was trained using the eligible features, and the model was employed on the hold out test set. The ROC AUC for the hold out test set was used to assess model performance. This process was repeated 10 times for each downsampling fraction to reduce selection bias in subsampling, and model performance was assessed with and without incorporating the FIT feature. The downsampling analysis showed a direct relationship between total number of samples used for training and performance on the hold out test set. When excluding the FIT feature, the median ROC AUC for HRAs versus all other categories increased from 0.55 (30% of training data) to 0.67 (100% of training data) (FIG. 17A). When including the FIT feature, median ROC AUC for HRAs versus all other categories increased from 0.72 (30% of training data) to 0.78 (100% of training data) (FIG. 17B).

Figure 18:
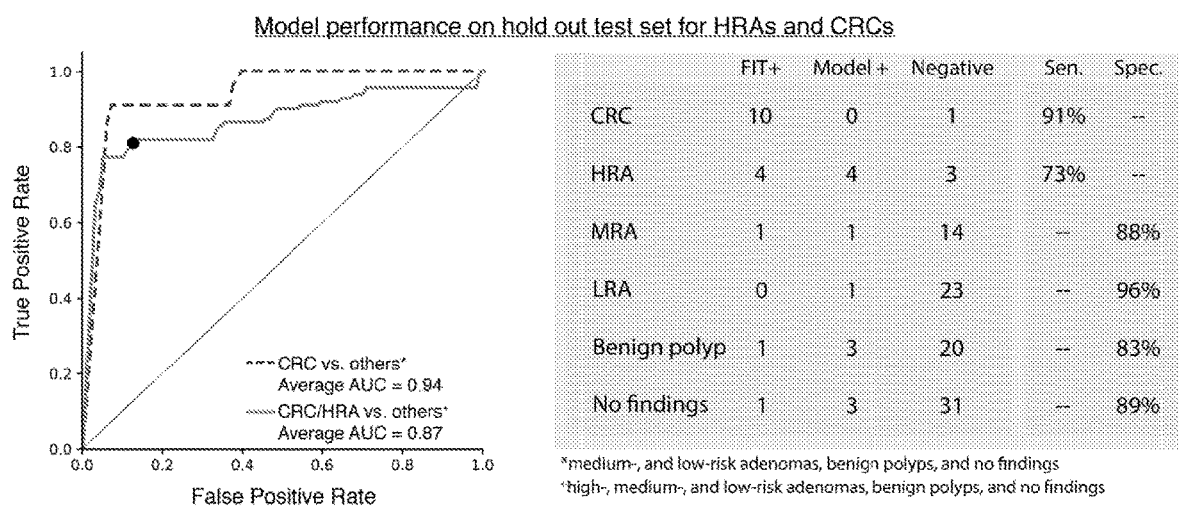
FIG. 18 is a graph showing model performance on all samples in the hold out test set, including 11 additional colorectal cancer (CRC) samples.

Final Accuracy: Continuing the above embodiment, the random forest model was also employed on the 11 retrospectively collected stool samples from CRC patients. Output from the model provided a prediction between 0-1 and a positive FIT forced model prediction to equal 1. Samples having a positive fecal immunochemical test (FIT+) or a positive model prediction (Model+) were considered positive and all other samples were considered negative. A ROC curve was plotted whereby only CRC samples were considered positive and other categories (HRAs, MRAs, LRAs, benign polyps, and no findings on a colonoscopy) were considered negative. Using all 121 samples in this supplemented hold out test set, this model attained a ROC AUC of 0.94. A separate ROC curve was plotted whereby CRC and HRA samples were considered positive and all other categories (MRAs, LRAs, benign polyps, and no findings on a colonoscopy) were considered negative. Using all 121 samples in this supplemented hold out test set, this model attained a ROC AUC of 0.87 (FIG. 18). A point on the ROC curve that maximized accuracy was selected to calculate sensitivity and specificity. At this point, the model demonstrated 91% sensitivity for CRC (n=11 samples) and a 73% sensitivity for HRAs (n=11 samples) at an 89% specificity (n=99 samples) (FIG. 18).

Figure 19:
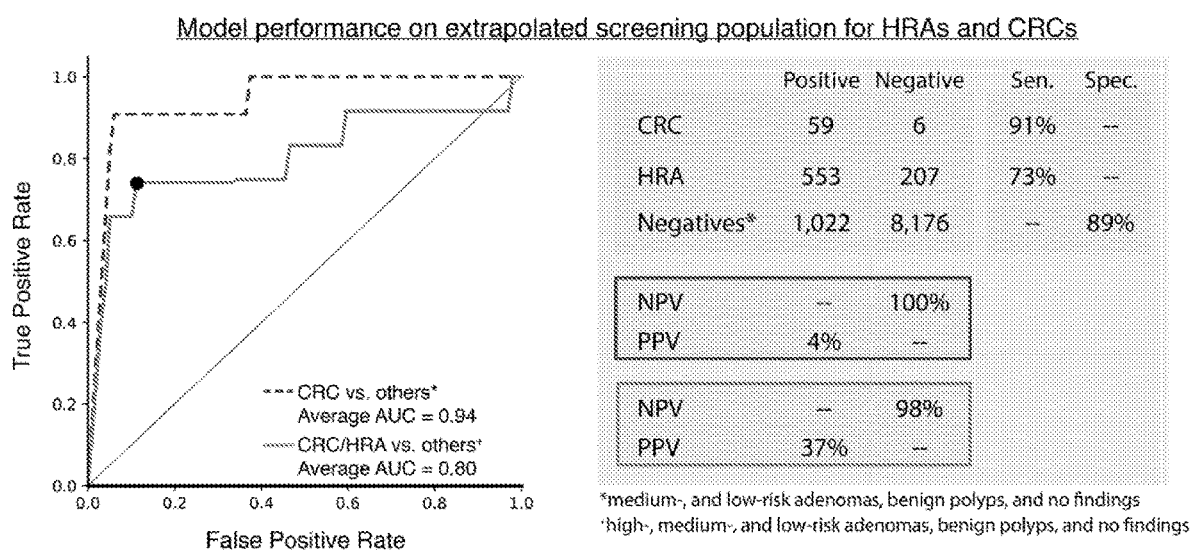
FIG. 19 is a graph showing model performance on all samples in the hold out test set, including 11 additional colorectal cancer (CRC) samples, extrapolated to a generalized screening population.

Extrapolation to Screening Population: To attain a better approximation of ultimate model performance, the accuracy profile observed on the supplemented hold out test set was extrapolated to the relative frequencies expected in a prospective screening population. ROC curves as described above were plotted to show model performance. When weighting cancer and HRAs to expected prevalence in a prospective screening population the model attained a ROC AUC of 0.80 for CRC and HRA samples versus all other categories (FIG. 19). Extrapolation of results onto a prospective screening population also enables the calculation of the blended sensitivity for neoplastic findings, negative predictive value (NPV), and positive predictive value (PPV). This extrapolated accuracy profile demonstrated a blended sensitivity for CRC and HRAs of 74%, a positive predictive value of 37%, and a negative predictive value of 98% (FIG. 19).

What is claimed is:

1. A method of detecting colorectal neoplasia in a subject, the method comprising:
    a) measuring an expression level for each of a plurality of stool-derived eukaryotic RNA biomarkers in eukaryotic nucleic acid extracted from a stool sample from the subject;
    b) comparing a first score comprising the aggregate of measured expression levels from step a) with a second score comprising the aggregate of measured expression levels of the plurality of stool-derived eukaryotic RNA biomarkers in a control from a population of healthy individuals,
    wherein an increase in the first score compared to the second score indicates that the subject has colorectal neoplasia, and
    c) administering a colonoscopy to the subject,
    wherein the plurality of stool-derived eukaryotic RNA biomarkers i) consists of ACY1, TNFRSF10B, EGLN2, SMAD4, KRAS, AREG, CDH1, and GAPDH or ii) consists of ACY1, TNFRSF10B, EGLN2, SMAD4, KRAS, AREG, and CDH1.

2. The method of claim 1, wherein the plurality of stool-derived eukaryotic RNA biomarkers consists of ACY1, TNFRSF10B, EGLN2, SMAD4, KRAS, AREG, and CDH1.

3. The method of claim 1, wherein the plurality of stool-derived eukaryotic RNA biomarkers consists of ACY1, TNFRSF10B, EGLN2, SMAD4, KRAS, AREG, CDH1, and GAPDH.

4. The method of claim 1, wherein the colorectal neoplasia is selected from the group consisting of colorectal cancer, high-risk adenoma, medium-risk adenoma, and low-risk adenoma.

5. The method of claim 1, wherein the nucleic acid comprises mRNA.

6. The method of claim 1, wherein the expression level is measured by nucleic acid sequencing, microarray sequencing, molecular barcoding, amplicon sequencing, probe capture, polymerase chain reaction (PCR), ddPCR, dPCR, RT-PCR, or RT-qPCR.

7. The method of claim 1, further comprising determining demographic information of the subject, wherein the demographic information comprises smoking status.

8. The method of claim 1, further comprising administering a fecal immunochemical test (FIT) to the subject.

9. A method of selecting a clinical plan for a subject having or at risk for colorectal neoplasia, the method comprising:
    a) measuring an expression level for each of a plurality of stool-derived eukaryotic RNA biomarkers in eukaryotic nucleic acid extracted from a stool sample from the subject;
    b) comparing a first score comprising the aggregate of measured expression levels from step a) with a second score comprising the aggregate of measured expression levels of the plurality of stool-derived eukaryotic RNA biomarkers in a control from a population of healthy individuals,
    wherein an increase in the first score compared to the second score indicates that the subject has colorectal neoplasia, and
    c) administering a colonoscopy to the subject,
    wherein the plurality of stool-derived eukaryotic RNA biomarkers i) consists of ACY1, TNFRSF10B, EGLN2, SMAD4, KRAS, AREG, CDH1, and GAPDH or ii) consists of ACY1, TNFRSF10B, EGLN2, SMAD4, KRAS, AREG, and CDH1.

10. The method of claim 9, wherein the plurality of stool-derived eukaryotic RNA biomarkers consists of ACY1, TNFRSF10B, EGLN2, SMAD4, KRAS, AREG, and CDH1.

11. The method of claim 9, wherein the plurality of stool-derived eukaryotic RNA biomarkers consists of ACY1, TNFRSF10B, EGLN2, SMAD4, KRAS, AREG, CDH1, and GAPDH.

12. The method of claim 9, wherein the colorectal neoplasia is selected from the group consisting of colorectal cancer, high-risk adenoma, medium-risk adenoma, and low-risk adenoma.

13. The method of claim 9, wherein the nucleic acid comprises mRNA.

14. The method of claim 9, wherein the expression level is measured by nucleic acid sequencing, microarray sequencing, molecular barcoding, amplicon sequencing, probe capture, polymerase chain reaction (PCR), ddPCR, dPCR, RT-PCR, or RT-qPCR.

15. The method of claim 9, further comprising determining demographic information of the subject, wherein the demographic information comprises smoking status.

16. The method of claim 9, further comprising administering a fecal immunochemical test (FIT) to the subject.

17. The method of claim 9, further comprising administering a treatment to the subject.

18. The method of claim 17, wherein the treatment comprises surgery, chemotherapy, radiation therapy, targeted therapy, immunotherapy, or any combination thereof.

19. A method of treating a colorectal neoplasia in a subject, the method comprising:
   a) measuring an expression level for each of a plurality of stool-derived eukaryotic RNA biomarkers in eukaryotic nucleic acid extracted from a stool sample from the subject;
   b) comparing a first score comprising the aggregate of measured expression levels from step a) with a second score comprising the aggregate of measured expression levels of the plurality of stool-derived eukaryotic RNA biomarkers in a control from a population of healthy individuals,
   wherein an increase in the first score compared to the second score indicates that the subject has colorectal neoplasia, and
   c) administering a colonoscopy to the subject,
   wherein the plurality of stool-derived eukaryotic RNA biomarkers i) consists of ACY1, TNFRSF10B, EGLN2, SMAD4, KRAS, AREG, CDH1, and GAPDH or ii) consists of ACY1, TNFRSF10B, EGLN2, SMAD4, KRAS, AREG, and CDH1.

20. The method of claim 19, wherein the plurality of stool-derived eukaryotic RNA biomarkers consists of ACY1, TNFRSF10B, EGLN2, SMAD4, KRAS, AREG, and CDH1.

21. The method of claim 19, wherein the plurality of stool-derived eukaryotic RNA biomarkers consists of ACY1, TNFRSF10B, EGLN2, SMAD4, KRAS, AREG, CDH1, and GAPDH.

22. The method of claim 19, wherein the colorectal neoplasia is selected from the group consisting of colorectal cancer, high-risk adenoma, medium-risk adenoma, and low-risk adenoma.

23. The method of claim 19, wherein the nucleic acid comprises mRNA.

24. The method of claim 19, wherein the expression level is measured by nucleic acid sequencing, microarray sequencing, molecular barcoding, amplicon sequencing, probe capture, polymerase chain reaction (PCR), ddPCR, dPCR, RT-PCR, or RT-qPCR.

25. The method of claim 19, wherein the treatment further comprises surgery.

26. The method of claim 19, wherein the treatment further comprises chemotherapy, radiation therapy, targeted therapy, immunotherapy, or any combination thereof.

27. The method of claim 19, further comprising determining demographic information of the subject, wherein the demographic information comprises smoking status.

28. The method of claim 19, further comprising administering a fecal immunochemical test (FIT) to the subject.

* * * * *